(12) United States Patent
Carrera Fabra et al.

(10) Patent No.: US 9,334,528 B2
(45) Date of Patent: May 10, 2016

(54) TEST CARTRIDGE WITH INTEGRATED TRANSFER MODULE

(71) Applicant: STAT-DIAGNOSTICA & INNOVATION, S.L., Barcelona (ES)

(72) Inventors: Jordi Carrera Fabra, Barcelona (ES); Anna Comengés Casas, Barcelona (ES); Rafael Bru Gibert, Barcelona (ES)

(73) Assignee: STAT-Diagnostica & Innovation, S.L., Barcelona (ES)

( * ) Notice: Subject to any disclaimer, the term of this patent is extended or adjusted under 35 U.S.C. 154(b) by 0 days.

(21) Appl. No.: 14/743,239

(22) Filed: Jun. 18, 2015

(65) Prior Publication Data

US 2015/0352551 A1 Dec. 10, 2015

Related U.S. Application Data

(62) Division of application No. 13/836,845, filed on Mar. 15, 2013, now Pat. No. 9,062,342.

(60) Provisional application No. 61/611,784, filed on Mar. 16, 2012.

(51) Int. Cl.
*G01N 15/06* (2006.01)
*G01N 33/00* (2006.01)
(Continued)

(52) U.S. Cl.
CPC .......... *C12Q 1/6806* (2013.01); *B01L 3/502715* (2013.01); *B01L 3/502738* (2013.01);
(Continued)

(58) Field of Classification Search
CPC ........ G01N 15/06; G01N 33/00; G01N 33/48
USPC .................. 422/50, 68.1, 554, 547, 559, 552; 436/43, 180
See application file for complete search history.

(56) References Cited

U.S. PATENT DOCUMENTS

| 4,587,223 | A | 5/1986 | Soini et al. |
| 4,680,275 | A | 7/1987 | Wagner et al. |

(Continued)

FOREIGN PATENT DOCUMENTS

| AU | 604684 B2 | 9/1987 |
| CA | 2082770 A1 | 8/1993 |

(Continued)

OTHER PUBLICATIONS

English language Abstract of European Patent No. EP 0 563 998 A1, European Patent Office, espacenet database-Worldwide (1998).

(Continued)

*Primary Examiner* — Brian J Sines
(74) *Attorney, Agent, or Firm* — Sterne, Kessler, Goldstein & Fox P.L.L.C.

(57) ABSTRACT

A system that includes a cartridge housing and a hollow transfer module, according to an embodiment is described herein. The cartridge housing further includes at least one sample inlet, a plurality of storage chambers, a plurality of reaction chambers, and a fluidic network. The fluidic network is designed to connect the at least one sample inlet, a portion of the plurality of storage chambers and the portion of the plurality of reaction chambers to a first plurality of ports located on an inner surface of the cartridge housing. The hollow transfer module includes a second plurality of ports along an outer surface of the transfer module that lead to a central chamber within the transfer module. The transfer module is designed to move laterally within the cartridge housing. The lateral movement of the transfer module aligns at least a portion of the first plurality of ports with at least a portion of the second plurality of ports.

11 Claims, 14 Drawing Sheets

(51) Int. Cl.
  *G01N 33/48*   (2006.01)
  *C12Q 1/68*    (2006.01)
  *C12M 3/00*    (2006.01)
  *G01N 33/53*   (2006.01)
  *B01L 3/00*    (2006.01)

(52) U.S. Cl.
  CPC .............. *C12M23/42* (2013.01); *C12Q 1/686* (2013.01); *G01N 33/53* (2013.01); *G01N 33/5304* (2013.01); *B01L 2200/026* (2013.01); *B01L 2200/027* (2013.01); *B01L 2200/028* (2013.01); *B01L 2200/04* (2013.01); *B01L 2200/16* (2013.01); *B01L 2300/0803* (2013.01); *B01L 2300/0877* (2013.01); *B01L 2400/0694* (2013.01)

(56) References Cited

U.S. PATENT DOCUMENTS

| | | | |
|---|---|---|---|
| 4,729,875 A | 3/1988 | Chandler | |
| 4,808,541 A | 2/1989 | Mikola et al. | |
| 4,855,930 A | 8/1989 | Chao et al. | |
| 4,923,819 A | 5/1990 | Fernandez et al. | |
| 5,061,076 A | 10/1991 | Hurley | |
| 5,116,576 A | 5/1992 | Stanley | |
| 5,144,139 A | 9/1992 | Hillman et al. | |
| 5,162,237 A | 11/1992 | Messenger et al. | |
| 5,219,526 A | 6/1993 | Long | |
| 5,223,219 A | 6/1993 | Subramanian et al. | |
| 5,316,909 A | 5/1994 | Xu | |
| 5,397,539 A | 3/1995 | Hayashi et al. | |
| 5,464,773 A | 11/1995 | Melendez et al. | |
| 5,637,509 A | 6/1997 | Hemmilä et al. | |
| 5,638,828 A | 6/1997 | Lauks et al. | |
| 5,744,096 A | 4/1998 | Jones et al. | |
| 5,961,925 A * | 10/1999 | Ruediger et al. | 422/537 |
| 5,971,941 A | 10/1999 | Simons et al. | |
| 6,036,924 A | 3/2000 | Simons et al. | |
| 6,267,722 B1 | 7/2001 | Anderson et al. | |
| 6,391,541 B1 | 5/2002 | Petersen et al. | |
| 6,431,476 B1 | 8/2002 | Taylor et al. | |
| 6,432,366 B2 * | 8/2002 | Ruediger et al. | 422/129 |
| 6,432,694 B1 | 8/2002 | Malmqvist | |
| 6,455,287 B1 | 9/2002 | Jem | |
| 6,472,220 B1 | 10/2002 | Simons et al. | |
| 6,488,896 B2 | 12/2002 | Weigl et al. | |
| 6,531,095 B2 | 3/2003 | Hammer et al. | |
| 6,552,784 B1 | 4/2003 | Dietz et al. | |
| 6,632,662 B1 | 10/2003 | Broyer et al. | |
| 6,656,428 B1 | 12/2003 | Clark et al. | |
| 6,660,472 B1 | 12/2003 | Santoro at al. | |
| 6,699,718 B1 | 3/2004 | Bruegger | |
| 6,830,936 B2 | 12/2004 | Anderson et al. | |
| 6,867,051 B1 | 3/2005 | Anderson et al. | |
| 6,905,585 B2 | 6/2005 | Goncalves | |
| 6,942,169 B2 | 9/2005 | Sparks | |
| 6,966,880 B2 | 11/2005 | Boecker et al. | |
| 7,097,981 B1 | 8/2006 | Gicquel et al. | |
| 7,101,509 B2 | 9/2006 | Chang et al. | |
| 7,220,595 B2 | 5/2007 | Nugent et al. | |
| 7,223,363 B2 | 5/2007 | McNeely et al. | |
| 7,232,109 B2 | 6/2007 | Driggs et al. | |
| 7,238,519 B2 | 7/2007 | Bellet et al. | |
| 7,297,151 B2 | 11/2007 | Boecker et al. | |
| 7,419,821 B2 | 9/2008 | Davis et al. | |
| 7,509,232 B2 | 3/2009 | Seher et al. | |
| 7,537,730 B2 | 5/2009 | Colin et al. | |
| 7,553,453 B2 | 6/2009 | Gu et al. | |
| 7,604,592 B2 | 10/2009 | Freeman et al. | |
| 7,622,083 B2 | 11/2009 | Amirkhanian et al. | |
| 7,666,687 B2 | 2/2010 | Webster et al. | |
| 7,723,095 B2 | 5/2010 | Cleuziat et al. | |
| 7,771,658 B2 | 8/2010 | Larsen | |
| 7,803,318 B2 | 9/2010 | Hübner et al. | |
| 7,824,614 B2 | 11/2010 | Tanaami | |
| 7,887,750 B2 | 2/2011 | Blatt et al. | |
| 7,887,751 B2 | 2/2011 | Mimura et al. | |
| 8,220,493 B2 * | 7/2012 | Easley et al. | 137/829 |
| 8,916,375 B2 * | 12/2014 | Landers et al. | 435/286.5 |
| 8,961,902 B2 * | 2/2015 | Falb et al. | 422/503 |
| 9,075,042 B2 * | 7/2015 | Cook et al. | |
| 2002/0106787 A1 | 8/2002 | Benn et al. | |
| 2003/0087454 A1 | 5/2003 | Schultz et al. | |
| 2003/0143120 A1 * | 7/2003 | Ruediger et al. | 422/99 |
| 2003/0162304 A1 | 8/2003 | Dority et al. | |
| 2004/0076990 A1 | 4/2004 | Picard et al. | |
| 2004/0214200 A1 | 10/2004 | Brown et al. | |
| 2005/0042137 A1 | 2/2005 | Petersen et al. | |
| 2005/0053952 A1 | 3/2005 | Hong et al. | |
| 2005/0089443 A1 | 4/2005 | Blanton et al. | |
| 2005/0176037 A1 | 8/2005 | Mastromatteo et al. | |
| 2006/0030038 A1 | 2/2006 | Taylor et al. | |
| 2006/0078929 A1 | 4/2006 | Bickel et al. | |
| 2006/0240403 A1 | 10/2006 | List et al. | |
| 2007/0053800 A1 | 3/2007 | Lehto | |
| 2007/0141605 A1 | 6/2007 | Vann et al. | |
| 2007/0152683 A1 | 7/2007 | Werner et al. | |
| 2008/0009043 A1 | 1/2008 | Yoo et al. | |
| 2008/0053543 A1 * | 3/2008 | Baier et al. | 137/625.15 |
| 2008/0057544 A1 | 3/2008 | Lem et al. | |
| 2008/0187924 A1 | 8/2008 | Korfhage et al. | |
| 2008/0199930 A1 | 8/2008 | Lee et al. | |
| 2008/0241890 A1 | 10/2008 | Gumbrecht et al. | |
| 2008/0268434 A1 | 10/2008 | Nurmi et al. | |
| 2009/0104076 A1 | 4/2009 | Staab | |
| 2009/0176314 A1 | 7/2009 | Steinboeck et al. | |
| 2009/0298059 A1 | 12/2009 | Gumbrecht et al. | |
| 2010/0068781 A1 | 3/2010 | Rajagopal et al. | |
| 2010/0099178 A1 | 4/2010 | Stolarchuk | |
| 2010/0104477 A1 | 4/2010 | Liu et al. | |
| 2010/0105577 A1 | 4/2010 | Dugan et al. | |
| 2010/0119414 A1 | 5/2010 | Eisenhardt et al. | |
| 2010/0173398 A1 | 7/2010 | Peterman | |
| 2010/0264155 A1 | 10/2010 | Harder et al. | |
| 2010/0285479 A1 | 11/2010 | Jenison | |
| 2010/0297645 A1 | 11/2010 | Pierik et al. | |
| 2010/0321004 A1 | 12/2010 | Lauks et al. | |
| 2010/0323919 A1 | 12/2010 | Chen et al. | |
| 2010/0331522 A1 | 12/2010 | Irvine et al. | |
| 2011/0008907 A1 | 1/2011 | Patno et al. | |
| 2011/0250680 A1 | 10/2011 | Broyer et al. | |
| 2014/0299221 A1 * | 10/2014 | Lopez et al. | 141/1 |

FOREIGN PATENT DOCUMENTS

| | | |
|---|---|---|
| CA | 1338167 C | 3/1996 |
| CN | 1166875 A | 12/1997 |
| CN | 101098956 A | 1/2008 |
| EP | 0 324 323 A1 | 7/1989 |
| EP | 0 515 211 A2 | 11/1992 |
| EP | 0 563 998 B1 | 10/1993 |
| EP | 1 080 785 A1 | 3/2001 |
| EP | 1 203 959 A1 | 5/2002 |
| EP | 1 385 006 A2 | 1/2004 |
| EP | 1 391 241 A1 | 2/2004 |
| EP | 1 878 496 A1 | 1/2008 |
| EP | 2 015 067 A1 | 1/2009 |
| EP | 2 182 345 A1 | 5/2010 |
| EP | 2 187 210 A1 | 5/2010 |
| EP | 2 191 900 A1 | 6/2010 |
| EP | 2 192 411 A1 | 6/2010 |
| FR | 2 826 454 A1 | 12/2002 |
| FR | 2 939 445 A1 | 6/2010 |
| GB | 2 432 420 A | 5/2007 |
| GB | 2 440 470 A | 1/2008 |
| JP | 2006-078265 A | 3/2006 |
| KR | 2008-0029233 A | 4/2008 |
| WO | WO 87/02708 A1 | 5/1987 |
| WO | WO 88/02784 A1 | 4/1988 |
| WO | WO 88/07670 A2 | 10/1988 |
| WO | WO 89/04375 A1 | 5/1989 |
| WO | WO 90/00550 A1 | 1/1990 |
| WO | WO 90/00623 A1 | 1/1990 |

(56) References Cited

FOREIGN PATENT DOCUMENTS

| | | |
|---|---|---|
| WO | WO 90/02938 A1 | 3/1990 |
| WO | WO 92/14841 A1 | 9/1992 |
| WO | WO 93/11433 A1 | 6/1993 |
| WO | WO 96/09553 A1 | 3/1996 |
| WO | WO 98/50147 A1 | 11/1998 |
| WO | WO 00/72970 A1 | 12/2000 |
| WO | WO 01/26813 A2 | 4/2001 |
| WO | WO 01/36666 A1 | 5/2001 |
| WO | WO 02/16652 A2 | 2/2002 |
| WO | WO 02/16652 A3 | 2/2002 |
| WO | WO 0218902 A1 | 3/2002 |
| WO | WO 03076937 A2 | 9/2003 |
| WO | WO 03094712 A3 | 11/2003 |
| WO | WO 2004/042003 A2 | 5/2004 |
| WO | WO 2004/078233 A3 | 9/2004 |
| WO | WO 2004/113874 A2 | 12/2004 |
| WO | WO 2005/094981 A1 | 10/2005 |
| WO | WO 2005/106023 A1 | 11/2005 |
| WO | WO 2005/107594 A2 | 11/2005 |
| WO | WO 2006/005347 A1 | 1/2006 |
| WO | WO 2006/042907 A1 | 4/2006 |
| WO | WO 2006/069577 A1 | 7/2006 |
| WO | WO 2006/122310 A2 | 11/2006 |
| WO | WO 2006/125767 A1 | 11/2006 |
| WO | WO 2007/005973 A3 | 1/2007 |
| WO | WO 2007/016866 A1 | 2/2007 |
| WO | WO 2007/075922 A2 | 7/2007 |
| WO | WO 2007/078850 A2 | 7/2007 |
| WO | WO 2008/030433 A2 | 3/2008 |
| WO | WO 2008/037989 A2 | 4/2008 |
| WO | WO 2008/060604 A3 | 5/2008 |
| WO | WO 2008/061165 A3 | 5/2008 |
| WO | WO 2008/101196 A1 | 8/2008 |
| WO | WO 2008/110019 A1 | 9/2008 |
| WO | WO 2008/140568 A2 | 11/2008 |
| WO | WO 2009/019448 A2 | 2/2009 |
| WO | WO 2009/019452 A1 | 2/2009 |
| WO | WO 2009/027935 A2 | 3/2009 |
| WO | WO 2009/030340 A1 | 3/2009 |
| WO | WO 2009/038628 A2 | 3/2009 |
| WO | WO 2009/051821 A2 | 4/2009 |
| WO | WO 2009/077982 A1 | 6/2009 |
| WO | WO 2009/131677 A1 | 10/2009 |
| WO | WO 2009/131686 A2 | 10/2009 |
| WO | WO 2009/137244 A9 | 11/2009 |
| WO | WO 2009/143089 A1 | 11/2009 |
| WO | WO 2009/149115 A1 | 12/2009 |
| WO | WO 2010/005467 A3 | 1/2010 |
| WO | WO 2010/031026 A2 | 3/2010 |
| WO | WO 2010/047609 A1 | 4/2010 |
| WO | WO 2010/051251 A1 | 5/2010 |
| WO | WO 2010/064160 A1 | 6/2010 |
| WO | WO 2010/065967 A3 | 6/2010 |
| WO | WO 2010/072011 A1 | 7/2010 |
| WO | WO 2010/077159 A1 | 7/2010 |
| WO | WO 2010/080115 A2 | 7/2010 |
| WO | WO 2010/087999 A1 | 8/2010 |
| WO | WO 2010/141921 A1 | 12/2010 |
| WO | WO 2011/047494 A1 | 4/2011 |

OTHER PUBLICATIONS

English language Abstract of French Publication No. FR 2 826 454 A1, European Patent Office, espacenet database-Worldwide (2002).

English language Abstract of Japanese Patent Publication No. 2006-078265 A, Japanese Patent Office, Patent & Utility Model Gazette DB, Patent Abstract of Japan (2006).

English language Abstract of Korean Patent Application No. KR 2008-0029233 A, European Patent Office, espacenet database-Worldwide (2008).

English language Abstract of Chinese Patent Publication No. Cn 101098956A, published. Jan. 2, 2008, European Patent Office, espacenet database-Worldwide (listed as document FP2 on the accompanying form PTO/SB/08A), 2 pages.

\* cited by examiner

900

| Laterally translate a transfer module to align an inlet port of the transfer module to an outlet port of the first chamber | 902 |

↓

| Draw a sample from the first chamber into a transfer chamber via an applied first pressure differential | 904 |

↓

| Laterally translate a transfer module to align an inlet port of the transfer module to an outlet port of the second chamber | 906 |

↓

| Draw the sample from the transfer module into the second chamber via an applied second pressure differential | 908 |

```
┌─────────────────────────────────────────────┐
│ Laterally translate a transfer module to align a │  1002
│   structure on an outer surface of the transfer  │
│ module to at least a first port and a second port│
└─────────────────────────────────────────────┘
                      │
                      ▼
┌─────────────────────────────────────────────┐
│     Draw a sample from the first chamber to a     │  1004
│  second chamber via the structure aligned over   │
│          the first port and second port          │
└─────────────────────────────────────────────┘
                      │
                      ▼
┌─────────────────────────────────────────────┐
│   Draw the sample from the second chamber to a   │  1006
│      third chamber within the transfer module    │
└─────────────────────────────────────────────┘
```

Fig. 10

TEST CARTRIDGE WITH INTEGRATED TRANSFER MODULE

CROSS-REFERENCE TO RELATED APPLICATIONS

This application is a divisional of U.S. application Ser. No. 13/836,845 filed on Mar. 15, 2013, which claims the benefit under 35 U.S.C. §119(e), to provisional application No. 61/611,784 filed on Mar. 16, 2012, the disclosures of which are each incorporated by reference herein in their entirety.

BACKGROUND

1. Field

Embodiments of the present invention relate to the field of clinical diagnostic tools.

2. Background

Given the complexity of the automation of molecular testing and immunoassay techniques, there is a lack of products that provide adequate performances to be clinically usable in near patient testing settings. Typical molecular testing includes various processes involving the correct dosage of reagents, sample introduction, lysis of cells to extract DNA or RNA, purification steps, and amplification for its subsequent detection. Even though there are central laboratory robotic platforms that automate these processes, for many tests requiring a short turnaround time, the central laboratory cannot provide the results in the needed time requirements.

However, it is difficult to implement systems in a clinical setting that provide accurate, trustworthy results at a reasonable expense. Given the complicated nature of various molecular testing techniques, the results are prone to error if the testing parameters are not carefully controlled or if the environmental conditions are not ideal. For example, existing instrumentation for PCR techniques has experienced high entry barriers for clinical diagnosis applications due to the background generated by exogenous sources of DNA. In the case of specific tests of pathogens, the predominant source of contamination is a result of previous reactions carried out in pipettes, tubes, or general laboratory equipment. Additionally, the use of molecular techniques for detection of microbial pathogens can produce false negatives. The false negatives may result from, for example: improper disposal of agents that inhibit the Polymerase Chain Reaction (PCR) such as hemoglobin, urine or sputum; inefficient release of DNA from cells; or low efficiency in extraction and purification of DNA or RNA.

The fact that molecular techniques have exceptional sensitivity levels at concentrations lower than the previous reference methods makes it rather difficult to obtain clinically relevant conclusions, while avoiding erroneous calls with false positives. To minimize this problem, especially for the detection of pathogen microorganisms, the tests must have quantification capability. It has therefore become increasingly necessary to perform multiplexed assays and arrays of tests to consolidate enough data to make confident conclusions. As an example, one of the main limitations of existing PCR-based tests is the inability to perform amplifications of different target genes simultaneously. While techniques such as microarrays provide very high multiplexing capacity, their main limitation is the low speed in obtaining the results, which often have no positive impact on patient management.

BRIEF SUMMARY

A clinical diagnostic platform can integrate a variety of analytical testing processes to reduce errors, costs and testing time.

In an embodiment, a system includes a cartridge housing and a hollow transfer module. The cartridge housing further includes at least one sample inlet, a plurality of storage chambers, a plurality of reaction chambers, and a fluidic network. The fluidic network is designed to connect the at least one sample inlet, a portion of the plurality of storage chambers and the portion of the plurality of reaction chambers to a first plurality of ports located on an inner surface of the cartridge housing. The hollow transfer module includes a second plurality of ports along an outer surface of the transfer module that lead to a central chamber within the transfer module. The transfer module is designed to move laterally within the cartridge housing. The lateral movement of the transfer module aligns at least a portion of the first plurality of ports with at least a portion of the second plurality Of ports.

In an embodiment, a transfer module includes an inner housing enclosing a central chamber and a jacket formed around the inner housing. The jacket includes patterned ridges along the outer surface of the jacket. The patterned ridges are designed to create a plurality of valve regions along the outer surface of the jacket when the transfer module is placed within an enclosure that comes into contact with the patterned ridges. The jacket further includes a plurality of ports extending through the jacket and the inner housing into the central chamber. The plurality of ports are located within one or more of the plurality of valve regions created by the patterned ridges. One of the plurality of valve regions with a corresponding port extending into the central chamber is designed to be pressurized separately from other regions in the plurality of valve regions, such that the pressurization generates a fluid flow either into or out of the central chamber via one or more of the plurality of ports.

An example method is described. The method includes laterally translating a transfer module to align a first port of the transfer module having a central chamber to a port of the first chamber. The method further includes drawing a sample into the central chamber from the first chamber via a first pressure differential. Once the sample is in the central chamber, the method includes laterally translating the transfer module to align a second port of the transfer module to a port of a second chamber and drawing the sample into the second chamber from the central chamber via a second pressure differential.

Another example method is described. The method includes laterally translating a transfer module within a housing to align a structure on an outer surface of the transfer module with a first port associated with a first chamber and with a second port associated with a second chamber. The method further includes drawing a sample from the first chamber to the second chamber via at least the structure aligned over the first port and the second port. The method continues with drawing the sample from the second chamber to a third chamber located within the transfer module via a port through a wall of the transfer module.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

FIG. 1 displays a graphical representation of the test cartridge system, according to an embodiment.

FIGS. 2A-2D display various views of a test cartridge system, according to an embodiment.

FIGS. 3A-3D display various views of the inner housing of a transfer module, according to an embodiment.

FIGS. 4A-4C display three views of a jacket of the transfer module, according to an embodiment.

FIGS. 5A and 5B display graphical representations of a test cartridge system, according to an embodiment.

FIGS. 6A and 6B display various views of a test cartridge system, according to an embodiment.

FIGS. 7A-7F display various views of a transfer module, according to an embodiment.

FIGS. 8A and 8B display swabs within a test cartridge system, according to some embodiments.

FIG. 9 is a diagram illustrating a method performed by a test cartridge system, according to an embodiment.

FIG. 10 is a diagram illustrating a method performed by a test cartridge system, according to an embodiment.

Figure 1:
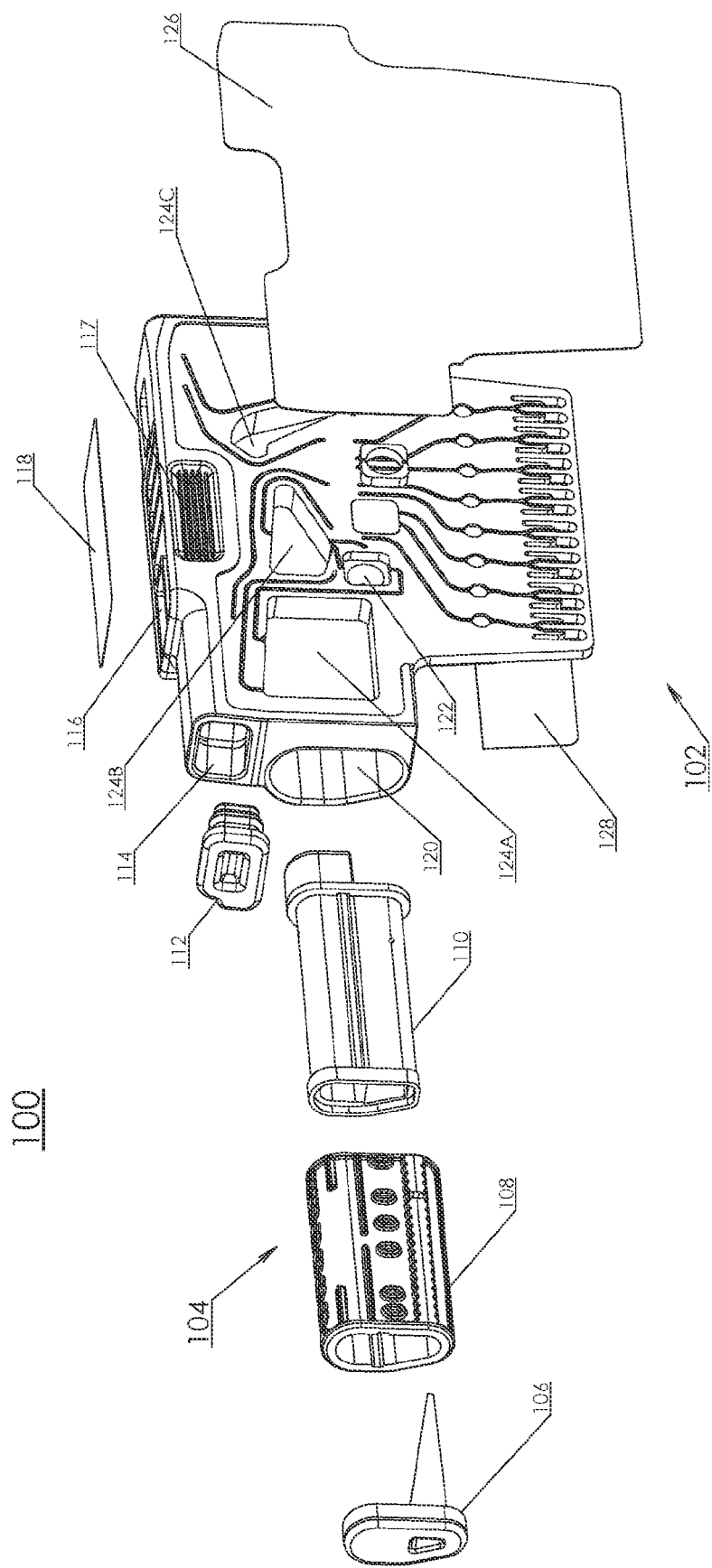

Embodiments of the present invention will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

Embodiments described herein relate to a test cartridge system for performing a variety of molecular, immunoassay, or biochemical tests, etc. In an embodiment, the test cartridge integrates all of the components necessary to perform such tests into a single, disposable package. The test cartridge may be configured to be analyzed by an external measurement system which provides data related to the reactions that take place within the test cartridge.

In one example, a single test cartridge may be used to perform a multiplexed immunoassay with a given sample. The test cartridge contains all of the necessary buffers, reagents, and labels held in sealed chambers integrated into the cartridge to perform the immunoassays.

In another example, a single test cartridge may be used to perform PCR. The DNA and/or RNA may be purified from the rest of a sample (lysate) via a membrane incorporated into the test cartridge. The sample may be extruded through the membrane while a separately stored elution liquid may remove the DNA and/or RNA and bring it into another chamber to begin the process of temperature cycling.

Any test such as those described above requires some form of liquid transport, to take place. In an embodiment, the test cartridge includes a moveable, hollow transfer module which includes a plurality of ports to align to ports along the sides of a cartridge housing. Liquid may be transferred between the other various chambers of the cartridge housing either into or out of the hollow transfer module by applying a pressure differential to the system. In one example, external actuators are utilized to apply the pressure differential.

One of the main limitations of molecular diagnostic instrumentation is the problem associated with contamination such as cross-contamination, carry-over contamination, etc. Embodiments described herein substantially eliminate by design the contamination of samples to the instrument.

In one embodiment, the test cartridge offers a self-contained liquid sealed during the manufacturing process. The reagents or the sample do not enter in contact with the environment or with any part of the instrument. This feature of the test cartridge is also important for many laboratories and hospitals to safely dispose of the products after their use.

Further details relating to the components of the test cartridge system are described herein with references made to the figures. It should be understood that the illustrations of each physical component are not meant to be limiting and that a person having skill in the relevant art(s) given the description herein would recognize ways to re-arrange or otherwise alter any of the components without deviating from the scope or spirit of the invention.

First Test Cartridge Embodiment

FIGS. 1-4 illustrate various views and components of a test cartridge system according to an embodiment. FIG. 1 illustrates a test cartridge system 100 that includes a cartridge housing 102 and a transfer module 104. Other components may be considered as well for inclusion in test cartridge system 100, such as an analyzer module or various active components such as pumps or heaters.

Transfer module 104 includes an inner housing 110, a jacket 108, and a lid 106. Jacket 108 is designed to fit around inner housing 110, according to an embodiment. In one example, inner housing 110 is made of a hard material such as metal or plastic, while jacket 108 is made of a compliant material such as rubber or soft plastic. In another example, both jacket 108 and inner housing 110 are made of a soft compliant material, which may be the same material or different materials. In another example, both jacket 108 and inner housing 110 are made via an overinjection process. Lid 106 is designed to seal the end of transfer module 104 to prevent leakage. Further details regarding the components of transfer module 104 are discussed later with reference to FIGS. 3 and 4.

Transfer module 104 is designed to be inserted into cartridge housing 102 via chamber bay 120. In one embodiment, transfer module 104 is configured to connect to an external actuator (not shown). The external actuator may laterally move transfer module 104 within cartridge housing 102 to align ports on transfer module 104 to ports on cartridge housing 102. In another embodiment, transfer module 104 is configured to move within cartridge housing 102 via operation of an external slider by a user.

Cartridge housing 102 includes a variety of fluidic channels, chambers, and reservoirs. For example, cartridge housing 102 may include a plurality of storage chambers 116 which may contain various buffers or other reagents to be used during an assay or PCR protocol. Storage chambers 116 may be pre-filled with various liquids so that the end user will not need to fill storage chambers 116 before placing test cartridge system 100 into an analyzer. Cartridge housing 102 may further include one or more processing chambers 124A-C connected to fluidic channels along a side of cartridge housing 102. Processing chambers 124A-C may be used for a variety of processing and/or waste applications. In one example, chamber 124A is a waste chamber, chamber 124B is an elution chamber for PCR protocols, and chamber 124C is a swab elution chamber. In an embodiment, cartridge housing 102 includes a grip structure 117 to provide easier handling of test cartridge system 100.

Samples are introduced into cartridge housing 102 via sample port 114, according to an embodiment. In one example, sample port 114 is dimensioned to completely receive the length of a common medical swab. Thus, the user may place the swab either up to a break-off point or completely within sample port 114, and subsequently seal the port with a port lid 112. In another example, sample port 114 receives solid, semi-solid, or liquid samples. In an embodiment, cartridge housing 102 includes more than one inlet to introduce samples.

Cartridge housing 102 may incorporate one or more useful structures for performing tests, such as filters, gels, membranes, etc. For example, cartridge housing 102 may include a membrane housed in cavity 122. In one embodiment, the membrane is coupled with the fluidic channels along the outside of cartridge housing 102. In another embodiment, the membrane may be disposed within any one of processing chambers 124A-C.

The various chambers and channels around cartridge housing 102 may be sealed via the use of covers 118, 126, and 128. The covers may be films capable of sealing the fluid within cartridge housing 102. In another example, the covers may be plastic sheets or any other means of sealing. In an example, one or more of the covers are transparent.

The integrated test cartridge system 100 allows a user to place a sample into, for example, sample port 114, then place test cartridge system 100 into an analyzer. In embodiments, the reaction steps to be performed including, for example, re-suspension lysing, purification, mixing, heating, binding, labeling and/or detecting can all be performed within test cartridge system 100 via interaction with the analyzer without any need for the end user to intervene. Additionally, since all of the liquids remain sealed within test cartridge system 100, after the test is completed, test cartridge system 100 may be removed from the analyzer and safely disposed of without contamination of the analyzer.

FIGS. 2A-D illustrate various views of cartridge housing 102, according to embodiments. The description of each view is set forth to describe features that may be present on cartridge housing 102, but should not be limiting as to the placement or dimensional properties of the features.

Figure 2A:
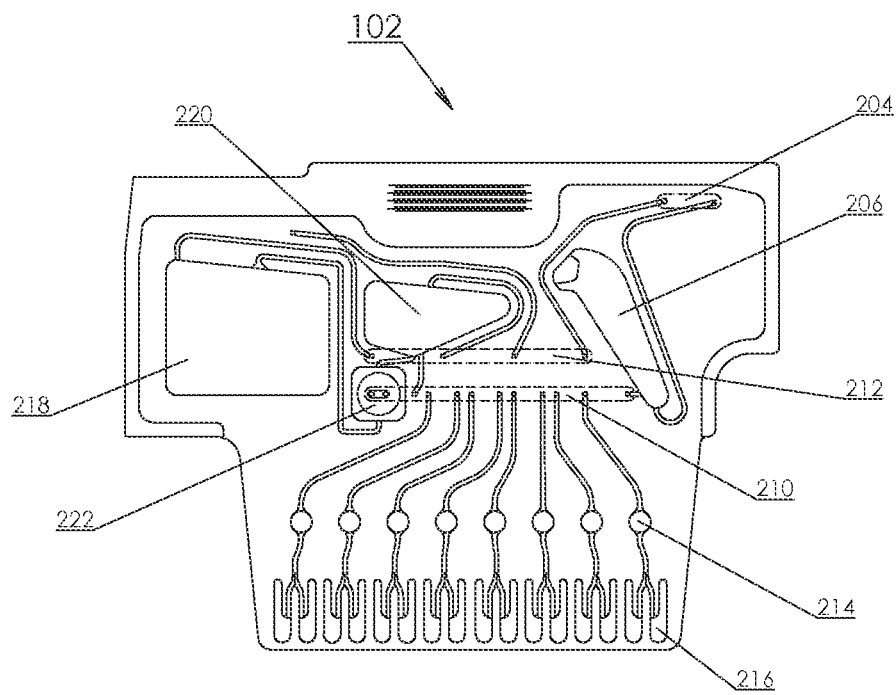

FIG. 2A provides an example of a side view of cartridge housing 102. As such, the view illustrates a plurality of chambers connected by a fluidic network and a series of ports which extend into cartridge housing 102. Each of these groups will be discussed in more detail herein.

The plurality of processing chambers may include a waste chamber 218, an elution chamber 220, and a swab elution chamber 206. Other types of chambers as would be contemplated by one having skill in the relevant art(s) given the description herein may also be included. Furthermore, the purpose of each chamber may be different than the names specified herein.

A plurality of reaction chambers 216 is also shown. Such chambers may be shaped similarly, for example, to a centrifuge tube. In one embodiment, liquid may be drawn into reaction chambers 216 to mix with reagents that have been pre-loaded into each reaction chamber. For example, each reaction chamber may be loaded with a different DNA probe, or real time PCR master mix, and liquid may be drawn into each reaction chamber to create distinct mixtures in each chamber. The reagents may be freeze-dried before being loaded, or freeze-dried into reaction chambers 216. In another embodiment, reaction chambers 216 are also used for sample detection. Thus, in one embodiment, reaction chambers 216 may also be considered to be detection chambers. Detection may occur using an external optical source and photodetector coupled to an analyzer in which test cartridge system 100 is placed. Thus, any walls or covers of reaction chambers 216 may be transparent to allow for optical detection. In one example, the photodetector measures absorbance through the liquid within the reaction chamber at one or more wavelengths. In another example, the photodetector measures a fluorescence signal generated from a fluorescent compound within the reaction chamber. In an embodiment, the fluorescence measurements are taken from beneath reaction chambers 216. Reaction chambers 216 may be adapted for other means of detection, e.g., electrochemical, electromechanical, surface plasmon resonance, etc.

A set of smaller channel enlargements 214 are observed upstream from reaction chambers 216, according to an embodiment. Channel enlargements 214 may act as liquid sensing areas. As such, channel enlargements 214 may be used along with an external optical probe to determine whether or not liquid is present within channel enlargements 214. This determination may be used to activate other functions of test cartridge system 100. In another embodiment, channel enlargements 214 may include integrated sensors, such as a patterned resistive sensor, to indicate the presence or flow rate of the fluid.

Various fluidic channels connect to each of the chambers or to other elements within cartridge housing 102. Each channel is also designed to terminate at a port which will interface with the ports or valve regions on transfer module 104. In an embodiment, cartridge housing 102 includes two main rows of ports such as a row of liquid ports 210, and a row of vent/suction ports 212. Liquid ports 210 allow fluid to flow to any of the chambers depicted in FIG. 2A, or to flow through a filter 222. Liquid ports 210 may act as either inlet ports for liquid to be drawn into transfer module 104 from cartridge housing 102, or as outlet ports for liquid to be expelled from transfer module 104 to the fluidic network of cartridge housing 102. Vent/suction ports 212 may be used to open a particular fluidic channel to the atmosphere so that liquid can be drawn into its corresponding chamber. For example, a vacuum pressure may be applied to the port illustrated on the far left of the row of vent/suction ports 212, which would allow for liquid to enter into waste chamber 218 via the second to the left port on the row of liquid ports 210. In another example, a vacuum pressure applied from the second to the left port on the row of vent/suction ports 212 would draw liquid from the third to the left liquid port into elution chamber 220. In another embodiment, vent/suction ports 212 may be opened to the atmosphere.

Other processing ports 204 can be observed leading into another section of cartridge housing 102. Processing ports 204 may lead into or out of an inner processing chamber. For example, the inner processing chamber may be a bead beater chamber for lysing any cells in the sample. In another example, a sample containing solid, semi-solid or liquid material may be placed directly into the inner processing chamber via a second sample inlet. The material may be homogenized or lysed by the inner processing chamber, and the resultant liquid sample may be drawn from the inner processing chamber to transfer module 104 via an inner port (not shown) of the inner processing chamber.

A port may be a small hole extending through the thickness of cartridge housing 102. In an embodiment, each of liquid ports 210 is designed to align to another port located on transfer module 104, which can move laterally between the various liquid ports 210. In an embodiment, each of vent/suction ports 212 is designed to align to a region around transfer module 104 which allows the port to be either vented to atmosphere or pressurized. The various ports may include a hydrophobic material or have a specific geometry so as to prevent leakage through the ports in the absence of any applied pressure.

Filter 222 may be integrated within the fluidic network as illustrated. As such, liquid may pass through filter 222 due to a pressure difference. Filter 222 may include, for example, a silicate matrix to be used for trapping nucleic acid sequences. In another example, filter 222 may be a membrane for extracting plasma from whole blood samples. Other filter types may be contemplated as well, such as a reverse-osmosis filter. In another example, filter 222 may include suitable materials for an affinity chromatography column to perform, for example, protein purification protocols.

Figure 2B:
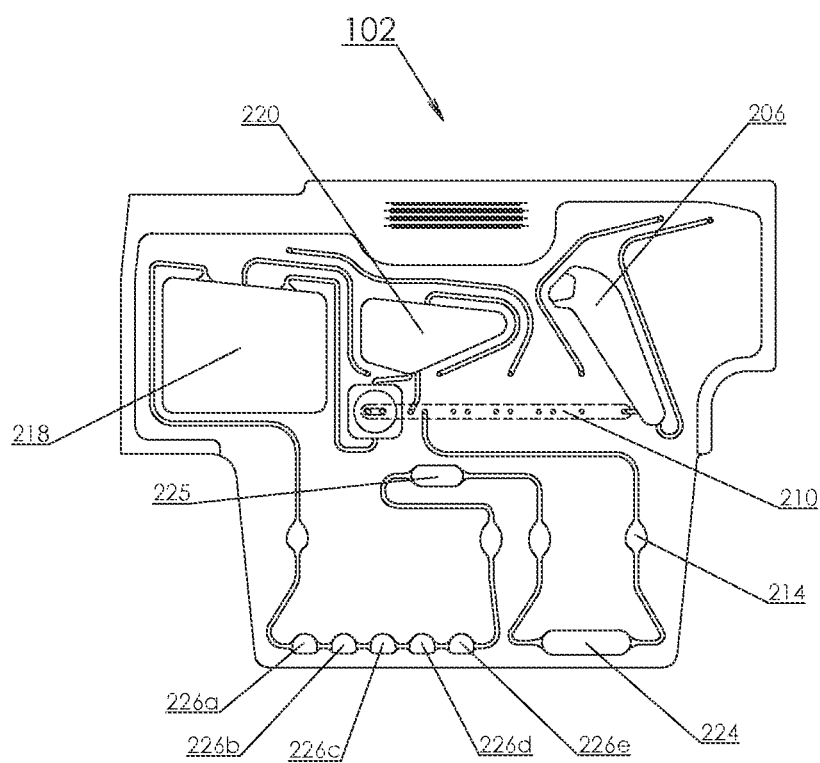

FIG. 2B illustrates another example embodiment of cartridge housing 102. This embodiment includes many of the same features as the example cartridge housing illustrated in FIG. 2A including waste chamber 218, elution chamber 220, and swab elution chamber 206. However, the fluidic network connected to liquid ports 210 now includes a reaction chamber 224, chamber 225 and a plurality of detection chambers 226a-e. In one example, a single fluidic path connects each of reaction chamber 224, chamber 225, and detection chambers 226a-e together. In another example, the fluidic path terminates at waste chamber 218. A series of channel enlargements 214 are illustrated as well and may serve the same purpose as those in the embodiment described above in FIG. 2A. The arrangement of chambers described in this embodiment may be useful for immunoassays or other types of binding affinity assays.

Reaction chamber 224 may contain reagents to be mixed with a sample before passing on to detection chambers 226a-e. The reagents may be first freeze-dried and placed, or freeze-dried into reaction chamber 224, and rehydrated upon contact with the liquid sample. Chamber 225 may contain a new set of freeze-dried reagents and may be utilized during PCR protocols to perform further amplification of the nucleic acid sequences. In another example, chamber 225 may contain further reagents to be mixed with the sample. Alternatively, chamber 225 may contain a filter or capture probes to separate certain compounds from the sample before it passes on to detection chambers 226a-e.

Detection chambers 226a-c are configured to allow for optical interrogation similar to reaction chambers 216 as described above in FIG. 2A. In one example, each detection chamber 226a-e contains an immobilized probe for performing various binding affinity assays. At least one wall of detection chambers 226a-e is made to be transparent to visible light for fluorescence measurements. In an example, the fluorescence measurements are taken from beneath detection chambers 226a-e.

Figure 2C:
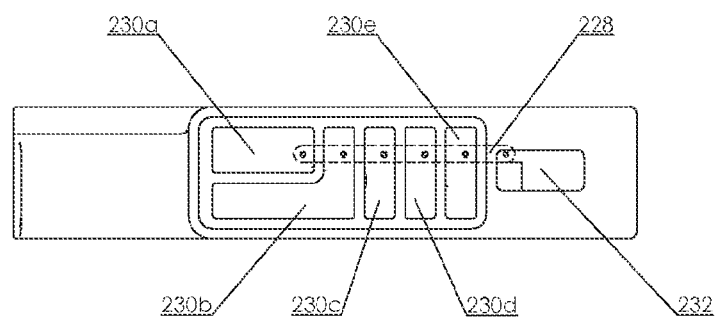

FIG. 2C illustrates a top view of cartridge housing 102, according to an embodiment. A plurality of storage chambers 230A-E are observed and may be similar to storage chambers 116 as described previously in FIG. 1. A sample inlet window 232 is also disposed at the top of cartridge housing 102, according to an embodiment. Sample inlet window 232 may be used to place samples into the inner processing chamber. For example, solid samples may need to be homogenized before testing can begin. These solid samples may be placed into sample inlet window 232 and enter directly into the inner processing chamber.

A row of inlet ports 228 are provided such that each port lies within a unique storage chamber, according to an embodiment. Solution stored within the various storage chambers 230A-E may be drawn down through a corresponding inlet port into transfer module 104 at the appropriate time during a testing procedure. Thus, transfer module 104 also has another port located at the top of transfer module 104 which can align with each of inlet ports 228. In an example, the lateral movement of transfer module 104 changes which port of the inlet ports 228 is aligned to the top port of transfer module 104. In another example, inlet ports 228 may lead directly to the fluidic network within cartridge housing 102 before reaching transfer module 104.

At least one of storage chambers 230A-E may be configured to receive a sample that has been placed into cartridge housing 102 via sample port 114. For example, storage chamber 230B may be dimensioned so as to receive a sample cotton swab. In another example, storage chamber 230B contains a solution to suspend a sample once the sample has been introduced.

Figure 2D:
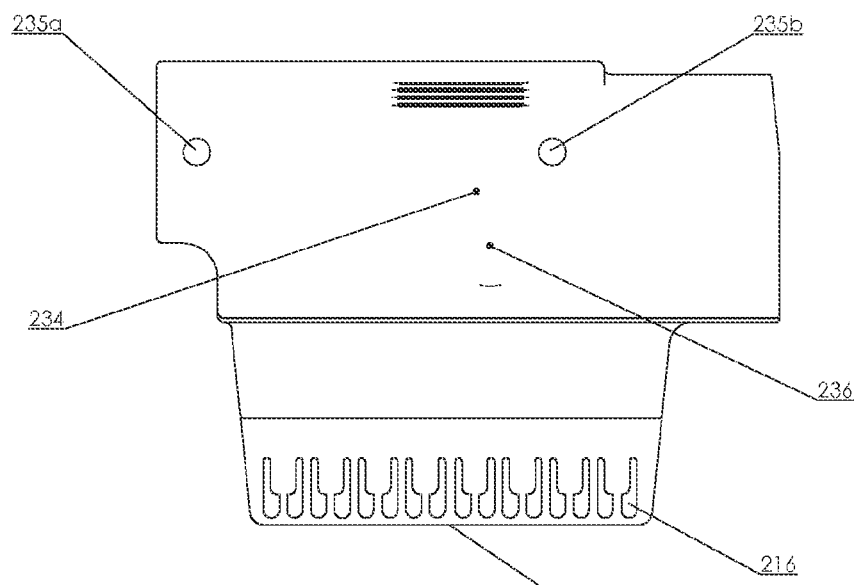

FIG. 2D illustrates a view of another side of cartridge housing 102 (opposite from the side illustrated in FIG. 2A). Additionally, cartridge housing 102 includes a pressurized port 236 and a vent port 234, according to an embodiment. Pressurized port 236 may be connected to an external pressure source, e.g. a vacuum pump, syringe pump, pressure pump, etc. In one example, the external pressure source is integrated with the analyzer into which test cartridge system 100 is placed. The pressure differential applied to the system via pressurized port 236 may be used to transport liquid throughout the various regions within cartridge housing 102 and transfer module 104. Vent port 234 may be configured to open to the atmosphere, according to an embodiment. As such, vent/suction ports 212 may lead to a region around transfer module 104 that is also coupled to vent port 234. In another example, a pressurized source is connected to pressurized port 236 to pull liquid through vent/suction ports 212. Any number of ports may be included for the purpose of pressurizing various regions in and around cartridge housing 102 and transfer module 104.

In one embodiment, cartridge housing 102 provides structures configured to center test cartridge system 100 within an automated analyzer. For example, a plurality of orifices 235a-b may be present on cartridge housing 102 to couple with corresponding pins on the analyzer to aid in centering test cartridge system 100 in regards to an external precision positioning system. Oblong protrusions may be used as well to center test cartridge system 100 within the automated analyzer. At the lower part of cartridge housing 102 in FIG. 2D, an optical access area 240 is disposed below reaction chambers 216, according to an embodiment. Optical access area 240 is configured to be substantially transparent to all wavelengths used during the optical detection process. In one example, each individual reaction chamber has its own optical access area. In another example, a single optical access area stretches across multiple reaction chambers 216.

A film or plurality of films may be placed over the series of reaction chambers 216. The films may be thin enough to still provide adequate sealing while also allowing for easier heating and/or cooling of the contents within reaction chambers 216 via an external source. For example, the films may be in contact with a surface that is thermally controlled by any one of or a combination of thermoelectric devices, resistive heaters, and forced air.

Figure 3A:
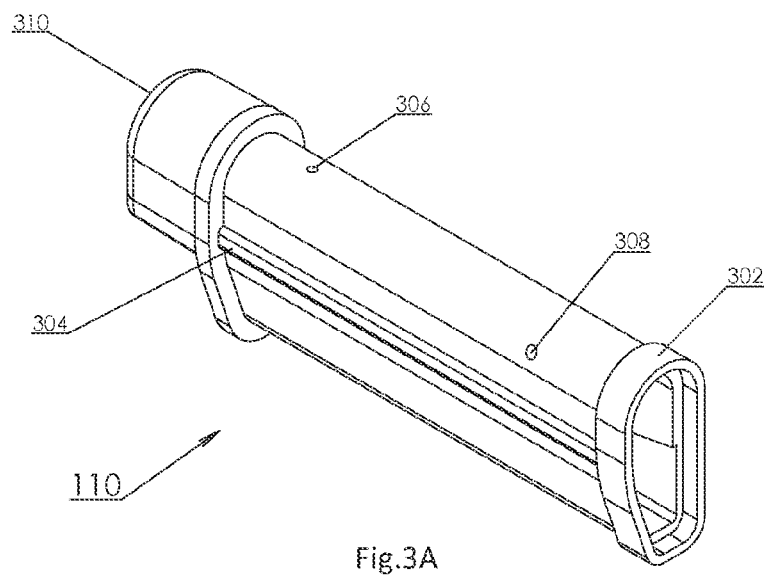

FIGS. 3A-D illustrate various views both around and inside inner housing 110 of transfer module 104, according to an embodiment. FIG. 3A depicts a perspective view of inner housing 110, according to an embodiment. Inner housing 110 is formed from case 302 which may be a rigid material. For example, case 302 may be a hard plastic or metal material. In another example, case 302 may be a flexible plastic material.

Inner housing 110 includes one or more ports which extend through the thickness of case 302. The ports may include a primary inlet port 306 and a transfer pressure port 308. In an embodiment, primary inlet port 306 aligns with various ones of inlet ports 228 as depicted in FIG. 2C.

In an embodiment, track 304 is used to hold valve jacket 108 in place around inner housing 110. Valve jacket 108 will be described separately in FIGS. 4A-C. Case 302 may also include a coupling region 310 to connect transfer module 104 to an actuator. The actuator may be motorized and apply a force upon transfer module 104 to cause movement. In another embodiment, coupling region 310 may be connected to any manner of structure which allows a user to apply a force to the structure and consequently move transfer module 104.

Figure 3B:
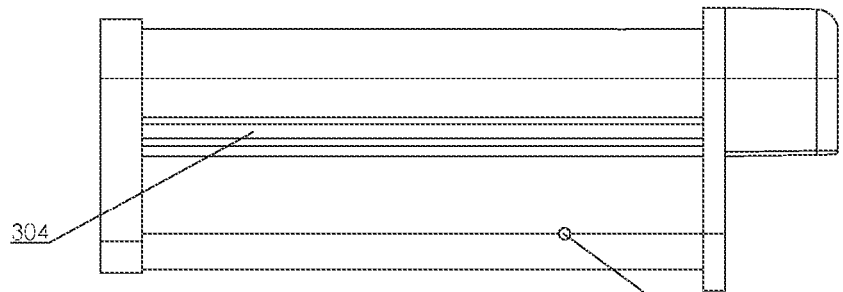

FIG. 3B illustrates a side view of inner housing 110. The view shown is the side which is facing away in FIG. 3A. A similar track 304 is illustrated on this side of inner housing 110 as well. In another embodiment, inner housing 110 only includes a single track structure. Also illustrated is a primary outlet port 312. In an embodiment, primary outlet port 312 aligns with various ones of liquid ports 210 as depicted in FIG. 2A. It should be appreciated that inner housing 110 may include any number of ports around the surface of case 302, and the illustrations shown here are not meant to be limiting in their placement and number of ports.

Figure 3C:
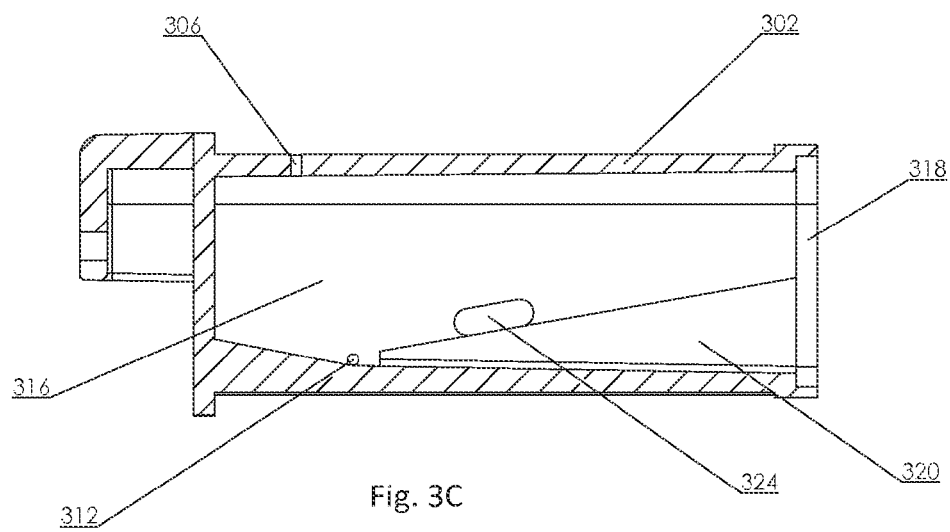

FIG. 3C illustrates a cross-section view of the interior of inner housing 110, according to an embodiment. Case 302 encloses transfer chamber 316. Also included is a chamber cover 318 to seal fluid or any other sample type within transfer chamber 316.

Primary outlet port 312 is illustrated at or near a lowest point within transfer chamber 316. The placement allows for any liquids within transfer chamber 316 to adequately drain through primary outlet port 312. To further facilitate adequate drainage, the inner walls of transfer chamber 316 are sloped downwards, according to an embodiment. In one example, one or more walls of transfer chamber 316 are sloped. In one example, a wedge 320 is disposed within transfer chamber 316 to provide a sloped surface.

In an embodiment, transfer chamber 316 contains a stirring element 324. For example, stirring element 324 may be a magnetic stir bar. Stirring element 324 may be used to effectively mix the contents of transfer chamber 316. In one example, stirring element 324 is excited via an external magnetic field. In an embodiment, cartridge housing 102 includes one or more magnets disposed along the movement path of transfer module 104. The presence of the magnets may induce a magnetic force upon stirring element 324, causing it to move within transfer chamber 316. In another example, stirring element 324 is physically coupled to an actuator configured to move stirring element 324.

Figure 3D:
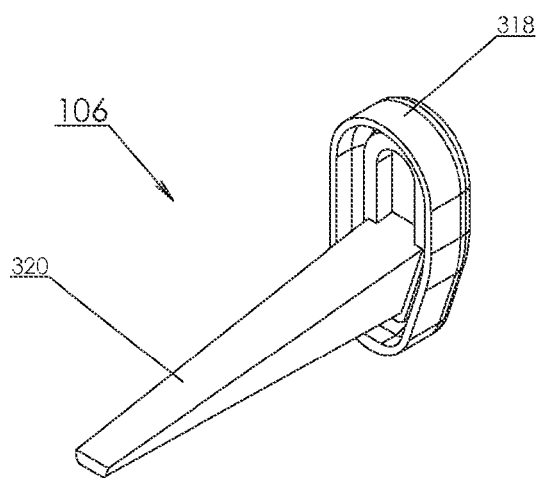

FIG. 3D illustrates a perspective view of lid 106, according to an embodiment. Lid 106 may include both chamber cover 318 as well as wedge 320 coupled to chamber cover 318. The integration of wedge 320 with chamber cover 318 allows for an easier manufacturing process.

Returning to FIG. 3A, the various ports disposed around inner housing 110 may be utilized for transferring liquid between various chambers of cartridge housing 102 and transfer chamber 316. In an example process, transfer module 104 is laterally moved to align primary inlet port 306 with one of the plurality of inlet ports 228 of cartridge housing 102. Once aligned, a vacuum pressure may be applied via transfer pressure port 308 which will draw liquid from the storage chamber of cartridge housing 102 into transfer chamber 316 of transfer module 104. Additional lateral movement of transfer module 104 aligns primary inlet port 306 with a different one of the plurality of inlet ports 228 of cartridge housing 102. A second applied vacuum pressure draws liquid from another storage chamber of cartridge housing 102 into transfer chamber 316. The two liquids within transfer chamber 316 may be further mixed if desired with stirring element 324. A third lateral movement of transfer module 104 aligns primary outlet port 312 with one of liquid ports 210 of cartridge housing 102. A positive pressure applied at transfer pressure port 308 expels liquid from transfer chamber 316 through primary outlet port 312 and into the fluidic network of cartridge housing 102 via the aligned liquid outlet port. It should be appreciated that many more liquid drawing and expelling procedures may be performed, and that liquid may also be drawn into transfer chamber 316 via primary outlet port 312.

Figure 4A:
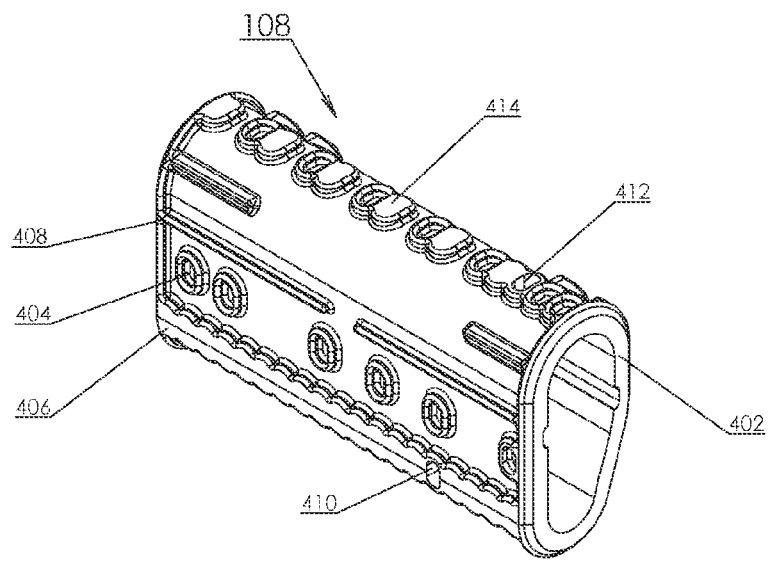
Figure 4B:
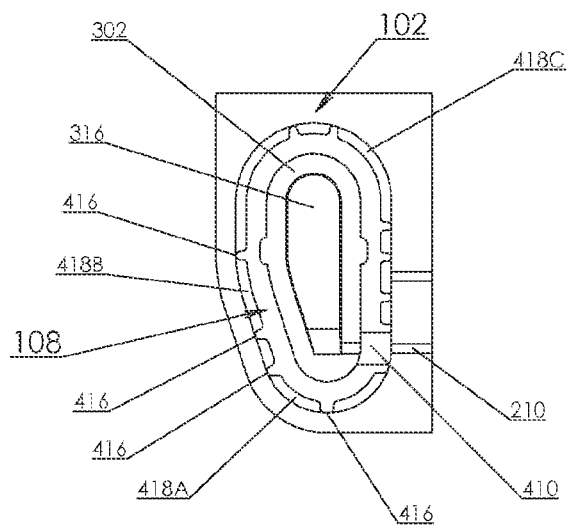
Figure 4C:
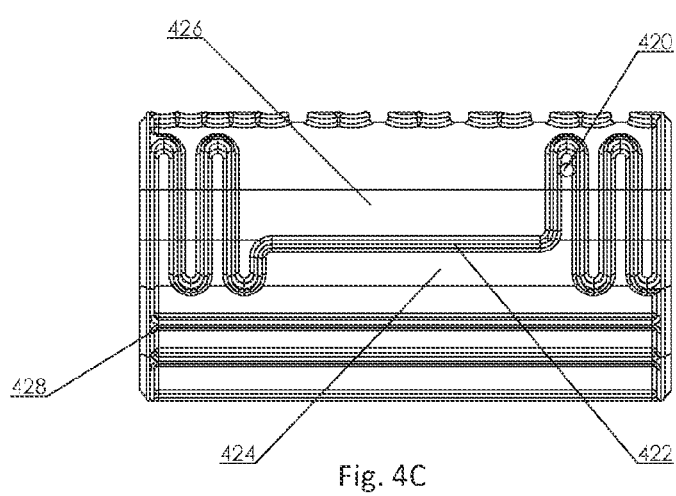
Figure 5A:
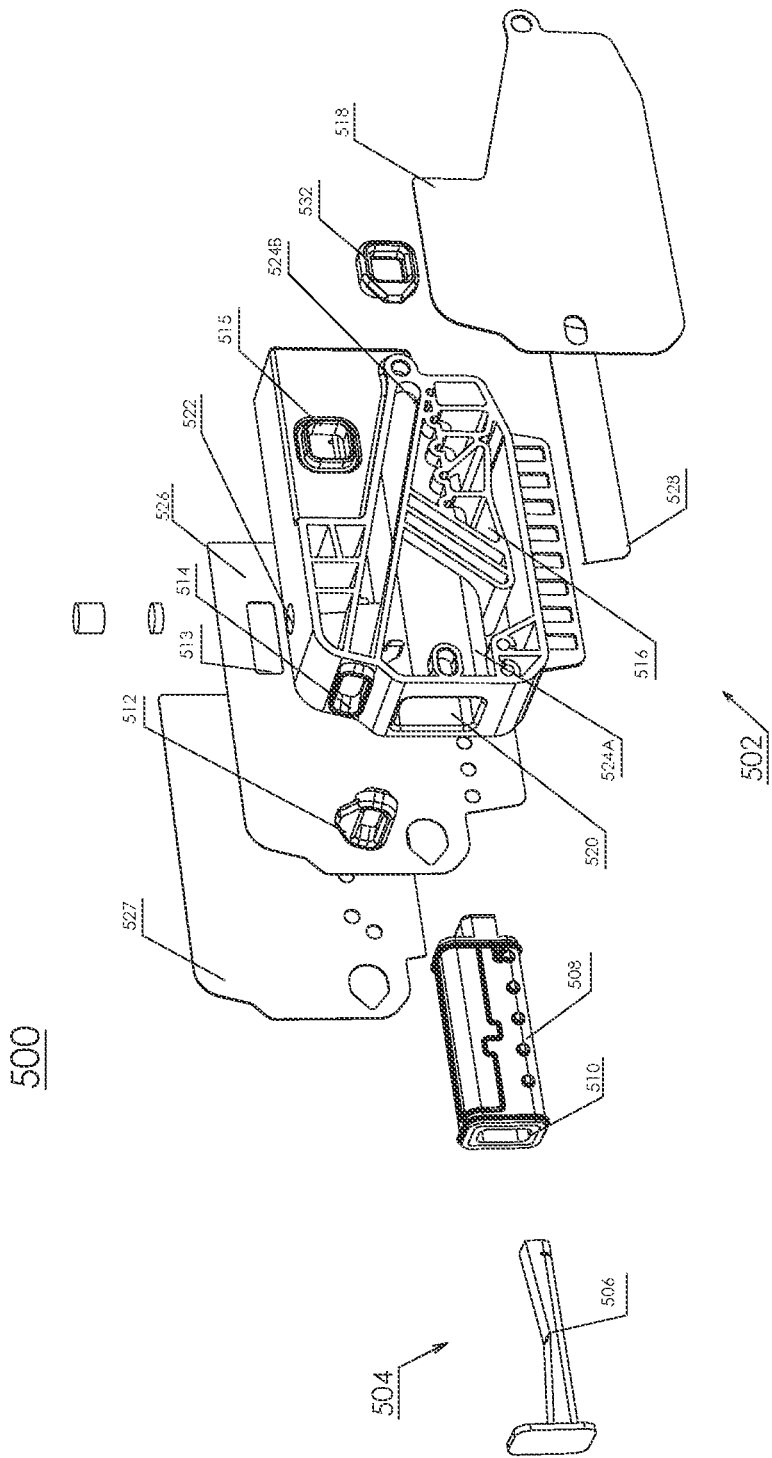
Figure 5B:
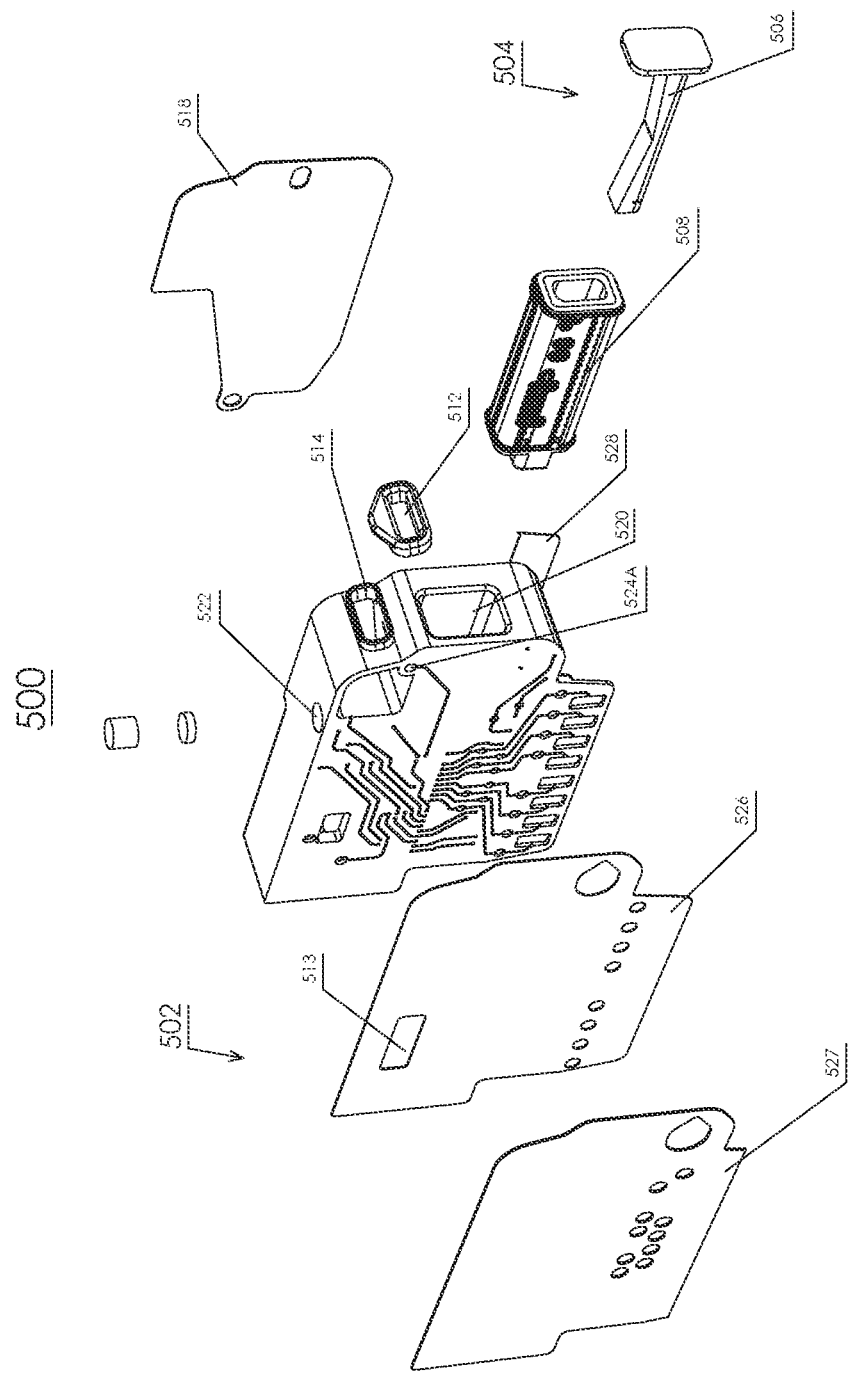

In order to control fluid flow along particular fluidic channels, as well as control which regions around the outside of transfer module 104 are pressurized, a valve system is implemented around inner housing 110. FIGS. 4A-C illustrate various views of valve jacket 108 disposed around inner housing 110.

FIG. 4A illustrates a perspective view of valve jacket 108, according to an embodiment. Valve jacket 108 includes a compliant casing 402 which fits around inner housing 110. Compliant casing 402 may be a flexible material such as rubber. In an embodiment, the outer surface of compliant casing 402 includes ports which extend through the thickness of compliant casing 402 and align with ports on inner housing 110. For example, a first port 410 may align with primary outlet port 312 while a second port 412 may align with primary inlet port 306.

The outer surface of compliant casing 402 may also include a variety of patterned ridges and shapes, according to an embodiment. For example, toroid ridges 404 along a side of valve jacket 108 may be aligned with various ones of the plurality of vent/suction ports 212. Additional toroid structures 414 are observed along the top of valve jacket 108. Solid toroid structures 414 may align over various ones of the plurality of inlet ports 228 to protect each port from being unwantedly pressurized. Solid toroid structures 414 are preferred for long term liquid storage in storage chambers 230a-e. Hollow toroid shapes provide the benefit of reducing friction as transfer module 104 moves within cartridge housing 102.

Other patterned ridges may be present as well. For example, scalloped ridges 406 may extend along a length of valve jacket 108 to seal any of the plurality of liquid ports 210 which are not aligned with first port 410. In another example, straight ridge 408 ensures a homogenous pressure on the inner surface of cartridge housing 102.

The various ridge patterns are designed to press against the inner walls of cartridge housing 102. This creates a plurality of regions around the outer surface of transfer module 104 which are sealed from one another. Thus, an applied pressure differential in one region will not affect the pressure in the other regions. This example design may be observed more clearly in FIG. 4B.

FIG. 4B illustrates a cross-section of transfer module 104 within transfer chamber 102, according to an embodiment. Inner housing 302 and valve jacket 108 of transfer module 104 are shown, as well as protrusions 416 off of valve jacket 108. Protrusions 416 may be similar to the ridges and toroid shapes as described previously in reference to FIG. 4A. Protrusions 416 press against the inner walls of cartridge housing 102 to create a plurality of valve regions, such as regions 418A-C, according to an embodiment. For example, region 418B is separated from regions 418A and 418C due to protrusions 416, and as such, could be pressurized separately from regions 418A and 418C.

In one example, region 418B is associated with pressurized port 236 (FIG. 2D) on a side of cartridge housing 102. An applied pressure differential via pressurized port 236 (FIG. 2D) will also pressurize region 418B, without pressuring the surrounding regions separated by protrusions 416.

The cross section view also illustrates how first port 410 of transfer module 104 may align with one of liquid ports 210 of cartridge housing 102. Protrusions 416 may surround port 410 to prevent leakage of fluid or unwanted pressurization of the port region.

FIG. 4C illustrates a side view of valve jacket 108, according to an embodiment. The side view depicted is the side facing away in FIG. 4A. Valve jacket 108 further includes a pressure port 420 which may be aligned with transfer pressure port 308 of inner housing 110, according to an embodiment. Pressure port 420 is disposed within a pressurized region 424 defined by various ridges, such as straight ridge 428 and serpentine ridge 422. Patterns and/or shapes of the ridges are not limited to those shown. Another region 426 exists on the other side of serpentine ridge 422, according to an embodiment. The regions described in reference to FIG. 4C may be considered similar to the regions described above with reference to FIG. 4B.

Pressurized region 424 is associated with a port of cartridge housing 102, according to an embodiment. For example, when transfer module 104 is located within cartridge housing 102, pressurized port 236 may be located within pressurized region 424. In one example, pressurized port is located below the middle, horizontal portion of serpentine ridge 422. As transfer module 104 translates within cartridge housing 102, pressurized region 424 remains associated with pressurized port 236, according to one example. In another example, translation of transfer module 104 may align vent port 234 within pressurized region 424 and pressurized port 236 within region 426 due to the serpentine shape associated with serpentine ridge 422. A pressure differential applied via a port aligned within pressurized region 424 will also apply the same pressure differential in transfer chamber 316 via pressure port 420. In another example, translation of transfer module 104 aligns pressurized port 236 with various regions around the outside surface of valve jacket 108.

Region 426 is also associated with a port of cartridge housing 102, according to an embodiment. For example, vent port 234 may be located within region 426, such as just above the middle, horizontal portion of serpentine ridge 422. In this example, region 426 is opened to atmospheric pressure. Alternatively, pressurized port 236 may be located within region 426, for example, between a bend of serpentine ridge 422. A vacuum pressure may be applied at pressurized port 236 which similarly pressurizes region 426.

Region 426 may wrap around to the other side of valve jacket 108 (the side depicted in FIG. 4A), according to an embodiment. Thus, the region surrounding toroid ridges 404 as well as toroid structures 414 may all be considered the same region as region 426. In an example embodiment, as transfer module 104 moves within cartridge housing 102 between discrete steps, toroid ridges 404 cover all but one of vent/suction ports 212, according to an embodiment. The one vent/suction port not covered by toroid ridges 404 is then subjected to either atmospheric pressure or a pressure differential that has been applied to region 426.

Second Test Cartridge Embodiment

FIGS. 5-8 illustrate various views and components of a test cartridge system according to another embodiment. FIGS. 5A-5B illustrate views of a blown out representation for a test cartridge system 500 that includes a cartridge housing 502 and a transfer module 504. Transfer module 504 has substantially the same function within the system as transfer module 104 from the first test cartridge embodiment. Both transfer modules 504, 104 move laterally within the system to line up ports on the exterior of the transfer module with ports on the sides of the housing 502, 102, according to some embodiments. Furthermore, transfer module 504 has a similar construction to transfer module 104 with an inner housing 510 surrounded by a jacket 508, and having an internal chamber capped by a lid 506. Further details of transfer module 504 are described later with reference to FIGS. 7A-D.

Housing 502 includes many of the same features as housing 102, according to some embodiments. For example, housing 502 includes a plurality of processing chambers 524a-b, a chamber bay 520 for receiving transfer module 504, and a sample port 514 with a port lid 512. In one example, chamber 524a is a waste chamber, and chamber 524b is a swab receptacle chamber. Sample port 514 leads into chamber 524b, which may be dimensioned to receive the length of a medical swab, according to one embodiment. Housing 502 also includes various covers 518, 526, 527, and 528 for sealing the various chambers and channels around housing 502, according to an embodiment. In one example, each of covers 526 and 518 are made from substantially the same material as housing 502. In an embodiment, any one of covers 526, 528, and 518 are substantially transparent. Cover 527 may be a material with a high thermal conductivity, e.g., aluminum foil, to allow for more efficient heat transfer to samples within housing 502. An opening 513 may be cut into cover 526 such that heat may be conducted more efficiently from cover 527 to an inner processing chamber of housing 502 via opening 513. The inner processing chamber may also have its own inlet with a cover 532. In an embodiment, housing 502 includes a top opening 522 for receiving various types filters to be placed into housing 502. In one example, solid phase extraction materials such as membranes or silica beads may be placed into a chamber of housing 502 via top opening 522. A plurality of openings are observed in both covers 526 and 527, according to some embodiments. The openings of cover 526 may align over various small chambers of housing 502 to, for example, allow more room for dry reagents to be placed into the small chambers. In another example, the openings of cover 527 may provide optical access to sensing areas of the channels of housing 502.

Housing 502 also includes an opening 515 into an inner processing chamber, according to an embodiment. Any type of sample, such as solid, semi-solid, or liquid samples, may be placed into the inner processing chamber via opening 515. Opening 515 may be capped by a cover 532 to prevent any leakage from samples placed into the inner processing chamber. Inner processing chamber may be, for example, a bead beater chamber for lysing cells or homogenizing a sample. Housing 502 may be dimensioned to incorporate various sizes of bead beater modules. In an embodiment, the bead beater modules within housing 502 accept liquid volumes ranging anywhere from 10 to 5000 microliters. In another embodiment, the accepted volumes of the bead beater modules range between 100 and 1000 microliters.

Figure 6A:
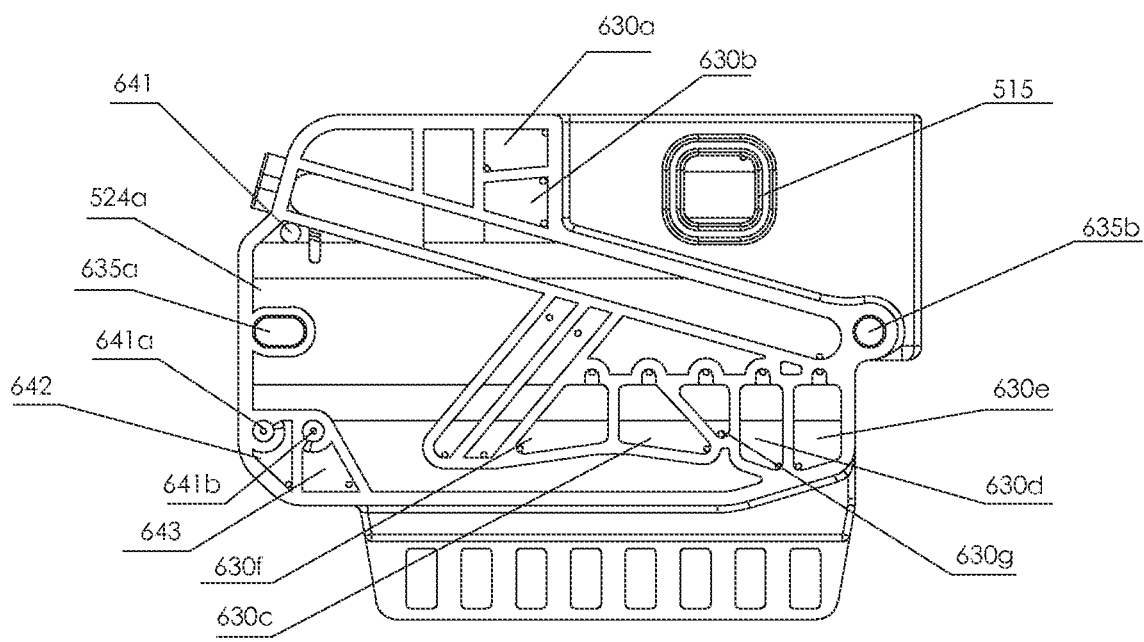
Figure 6B:
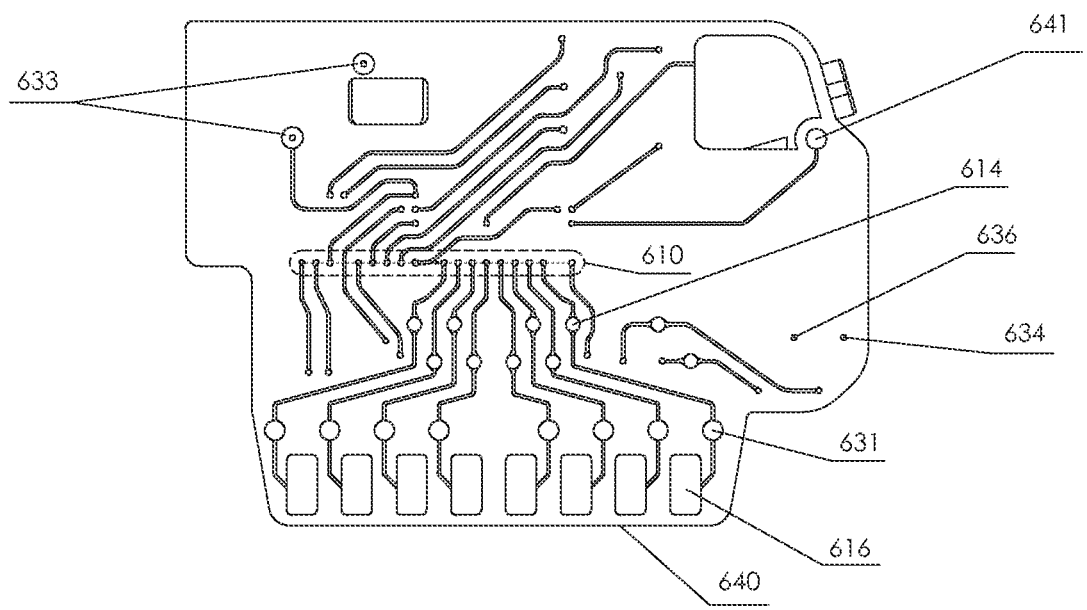

FIGS. 6A and 6B illustrate side views of housing 502 in more detail, according to some embodiments. FIG. 6A illustrates the various storage chambers on a side of housing 502. Housing 502 includes seven storage reservoirs 630a-g, according to an embodiment. Other numbers of storage reservoirs are also possible. It should also be understood that the illustrated shapes and sizes of the various storage reservoirs 630a-g are not intended to be limiting and could be altered to include virtually any shape and size. Each of the various storage reservoirs 630a-g may include two openings into the reservoir. A first opening may be coupled to a fluidic channel to transfer a fluid either into or out of the reservoir while a second opening may allow for venting of the reservoir to atmospheric pressure. The ability to vent a reservoir may allow the reservoir to empty more efficiently when fluid is drawn from it. Furthermore, air may not be trapped within the reservoir when fluid is moved into it if the air has the ability to escape out of a vent opening.

Also illustrated are two chambers, a first buffer chamber 642 and a second buffer chamber 643. Each buffer chamber may be used to help prevent liquid from exiting the fluidic infrastructure of the test cartridge system, according to an embodiment. For example, first buffer chamber 642 may be designed to hold any "spill-over" liquid that has accidently flown down a channel used for venting the system. The venting channel may also include a liquid sensing area. If liquid crosses the liquid sensing area, a sensor may be designed to shut off any applied forces that cause fluid to flow in order to stop the liquid before it can escape out of a venting port. Similarly, second buffer chamber 643 may be designed to hold any "spill-over" liquid that has accidently flown down a channel used for applying pressure to the system. In some embodiments, the applied pressure is a vacuum pressure for sucking the liquid through various channels and chambers of test cartridge system 500. The pressure channel may also include a liquid sensing area with an associated sensor designed to work in a similar way to the sensor described previously in the venting channel. Additionally, each port associated with first buffer chamber 642 and second buffer chamber 643 may include filters 641a and 641b, according to some embodiments. Filters 641a and 641b may be aerosol filters to prevent contamination to the rest of the system when using the ports for venting and/or pressurizing the system.

In an embodiment, housing 502 includes clamp points 635a and 635b to support housing 502 within a larger analyzer system. The test cartridge may be placed into an analyzer that includes components for heating and/or cooling the system, optically measuring certain chambers, providing a vacuum or pump source, and actuating the movement of transfer module 504. Housing 502 of test cartridge system 500 may be held in place within the analyzer via clamp points 635a and 635b so that housing 502 does not move while the various operations of the analyzer are being performed.

A waste passage 641 may also be included in housing 502 for guiding fluid and any other waste samples to a waste chamber, such as, for example, chamber 524a. The entrance into the waste chamber may be designed to only allow fluid to flow into the chamber and not out of the chamber.

FIG. 6B illustrates another example embodiment of the opposite side of housing 502. An example fluidic arrangement is presented with a plurality of ports 610 aligned for fluidic coupling with a port of transfer module 504. Also illustrated are pressure port 636 and vent port 634. Pressure port 636 may be connected to an external pressure source for applying either positive or negative pressure differentials throughout the system, according to an embodiment. Vent port 634 may either be open to the atmosphere or connect to another pressure source. For example, a positive pressure difference may be applied to one port while a negative pressure difference is applied to the other port to force a faster movement of liquid through the coupled channels of the system.

Housing 502 also includes reaction chambers 616 that may operate similarly to reaction chambers 216 described previously in regards to FIG. 2A. In an embodiment, various channels leading to reaction chambers 616 include a premixing chamber 631. Premixing chamber 631 may include dry chemicals, such as dried or lyophilized reagents. In another example, premixing chamber 631 includes dry chemistry beads or biological samples. Such biological or chemical compounds may be stored in premixing chamber 631 for long periods of time before use. The dimensions of premixing chamber 631 may be designed to specifically fit the size of a dry chemistry bead, usually on the order of a few millimeters in diameter, according to one embodiment. In one example, fluid drawn towards reaction chambers 616 mixes with the samples stored in premixing chamber 631. Various channels also include a sensor region 614, according to an embodiment. Sensor region 614 may be used to determine the presence and/or flow rate of the liquid within the corresponding channel. An external optical probe may be utilized with sensor region 614 to make the determination. In another example, integrated sensors, such as a resistive sensor, may indicate the presence or flow rate of the liquid. A control system may use the data output from sensor region 614 to activate various functions of test cartridge system 500, or to control the flow rate of the liquid within the respective channel having sensor region 614.

Also illustrated on the side of housing 502 are a plurality of frits 633. Each frit 633 may include various materials designed to filter or trap various particle sizes. In one example, frit 633 is a plastic material having a thin mesh with selectable pore sizes that may range anywhere between 0.1 microns to 500 microns. In one embodiment, frit 633 has a pore size of around 20 microns.

At the lower part of cartridge housing 502 in FIG. 6B, an optical access area 640 is disposed below reaction chambers 616, according to an embodiment. Optical access area 640 is designed to be substantially transparent to all wavelengths used during the optical detection process. In one example, each individual reaction chamber has its own optical access area. In another example, a single optical access area stretches across multiple reaction chambers 616. In one example, a photodetector measures absorbance through the liquid within reaction chamber 616 at one or more wavelengths. In another example, the photodetector measures a fluorescence signal generated from a fluorescent compound within reaction chamber 616. The fluorescence measurements may be taken from beneath reaction chambers 616 or from the side of reaction chambers 616. Reaction chambers 216 may be adapted for other means of detection, e.g., electrochemical, electromechanical, surface plasmon resonance, etc.

FIGS. 7A-7F provide various views in and around transfer module 504, according to some embodiments. Many of the general features of transfer module 504 are substantially similar to transfer chamber 104 of the first test cartridge embodiment. For example, both transfer modules include a compliant material wrapped around a harder inner housing, and have ports on the outside that lead inward towards a central chamber. However, the arrangement and design of certain features on transfer module 504 warrant further discussion, as is provided herein with regards to FIGS. 7A-7F.

Figure 7A:
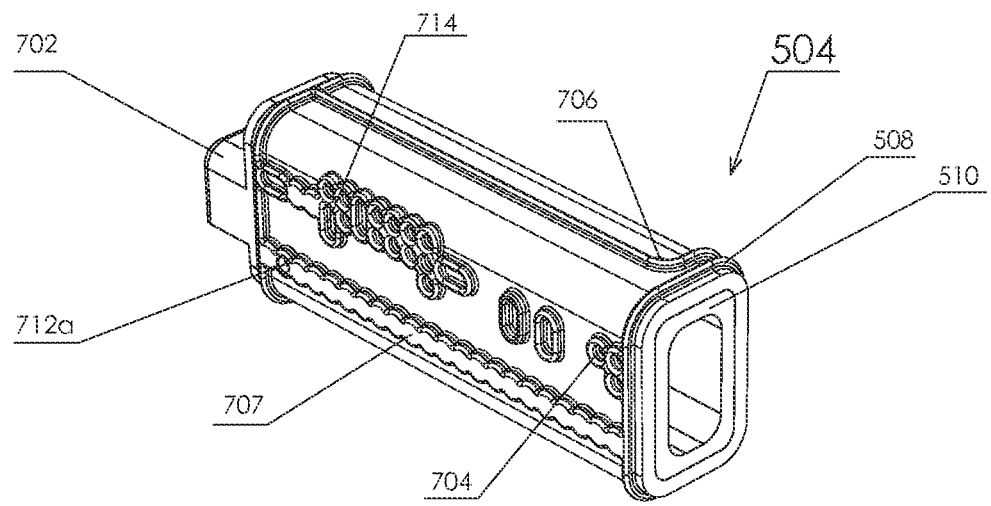
Figure 7B:
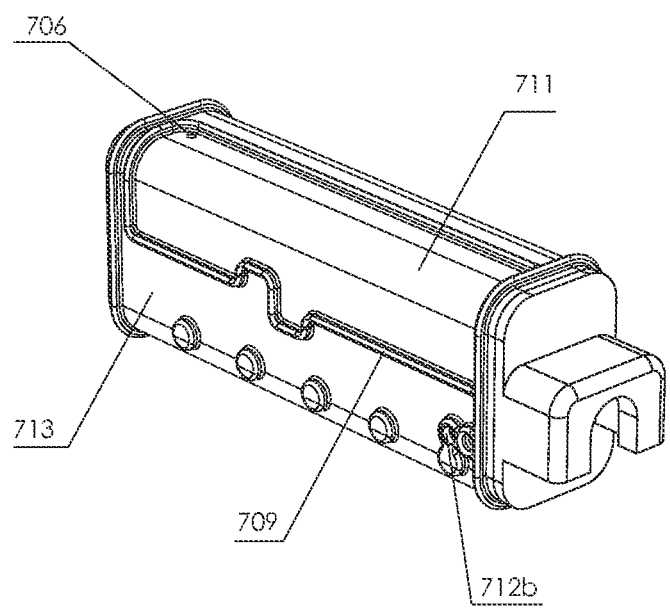

Two isometric schematic views from different sides of transfer module 504 are illustrated in FIGS. 7A and 7B, according to some embodiments. Transfer module 504 includes jacket 508 wrapped around an inner housing 510.

Transfer module 504 also includes two ports 712a and 712b. In an embodiment, each of ports 712a and 712b are disposed on a lower portion of transfer module 504. In one example, ports 712a and 712b are substantially across from one another. Transfer module 504 may also include a third port 706 along a top portion of transfer module 504. In an embodiment, ports 712a, 712b, and 706 lead into a central chamber inside transfer module 504. Either port 712a, 712b, and 706 may be used for coupling to various ports of housing 502 for fluid transfer. In another example, either port 712a, 712b, and 706 may be coupled to a pressurized source for applying a pressure difference to fluid within test cartridge system 500. In one embodiment, ports 712a and 712b are used for transferring fluid only while port 706 is used to pressurize or depressurize the central chamber of transfer module 504.

Transfer module 504 also includes a variety of patterned ridges and shapes, according to an embodiment. Similar to the patterned structures of jacket 108 on transfer module 104, the patterned regions on transfer module 504 may align to various ports of housing 502 and define various pressurized, or valve, regions around transfer module 504. For example, a toroid structure 704 may align over a port on housing 502 to seal that port. A cluster of toroid structures 714 is also provided, according to an embodiment. Cluster of toroid structures 714 may be arranged to align over various ports of housing 502 simultaneously based on a position of transfer module 504. In one embodiment, a toroid structure from cluster of toroid structures 714 acts as a fluidic bridge between at least two ports of housing 502. In an example, fluid may flow from one channel to another channel by flowing through two ports that are aligned over the same toroid structure. In this way, it is possible to move fluid through different channels of housing 502 without needing to pass the fluid through the central chamber of transfer module 504. Fluid may also still flow into and out of the central chamber of transfer module 504 via any of ports 712a, 712b, and 706, according to an embodiment.

Jacket 508 of transfer module 504 may also include various ridges 707 and 709. In an embodiment, ridge 707 is used to seal over various ports 610 of housing 502 while only a single port from ports 610 is aligned with port 712a. Ridge 709 may be used to differentiate between a plurality of regions, such as, for example, region 711 and 713. In one embodiment, regions 711 and 713 represent areas that may be pressurized separately. For example, region 711 may be pressurized via pressure port 636 due to the position of transfer module 504 within housing 502. Pressurizing region 711 may correspondingly pressurize the central chamber of transfer module 504 via port 706 and draw liquids into, or expel liquid from, the central chamber of transfer module 504.

Also illustrated on transfer module 504 is a coupling region 702 for connecting transfer module 504 to an actuator, according to an embodiment. The actuator may be designed to laterally translate transfer module 504 within housing 502 as substantially similar to the previously described first test cartridge embodiment.

Figure 7C:
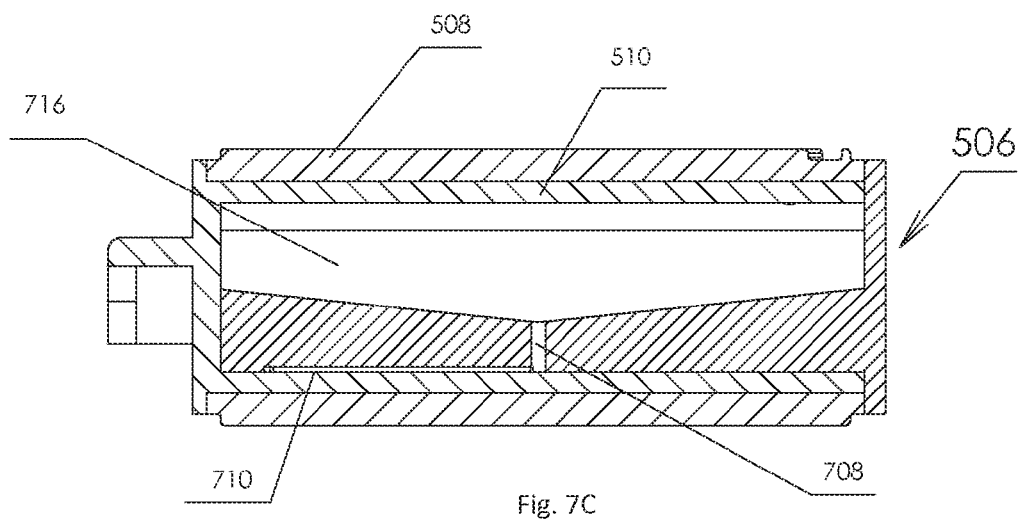

FIG. 7C illustrates a cross section view of transfer module 504 along a length of transfer module 504, according to an embodiment. Transfer module 504 includes a central chamber 716. Lid 506 is used to seal the end of central chamber 716. In one embodiment, lid 506 is designed to be removable. Lid 506 extends into central chamber 716 to provide sloped surface(s) to help drain any liquids within central chamber 716, according to one embodiment. A hole 708 is disposed substantially in the middle of lid 506 within central chamber 716 for transferring liquid to/from central chamber 716 from/ to other areas of housing 502. A transfer channel 710 may bring the liquid towards either or both of ports 712a and 712b.

Figure 7D:
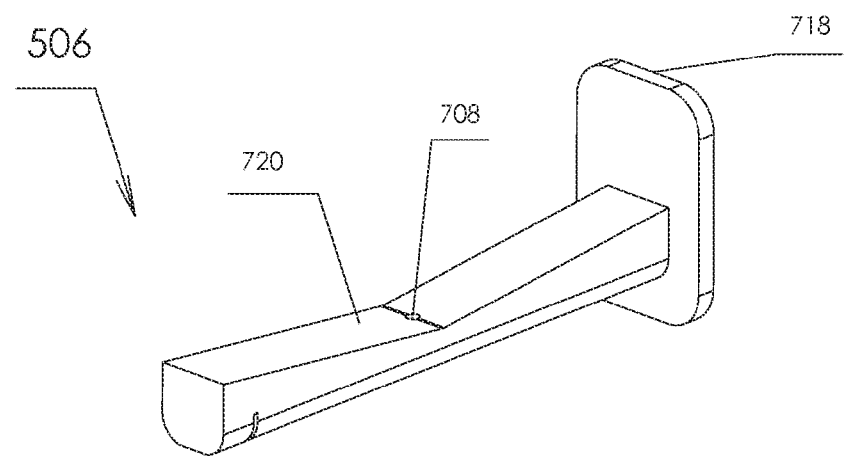

FIG. 7D provides a view of lid 506 that includes a panel 718 and a sloped structure 720, according to an embodiment. Panel 718 may be used to seal the end of central chamber 716 while sloped structure 720 provides a sloped surface to, for example, facilitate movement of liquid samples within central chamber 716 towards either port 712a or 712b. Hole 708 is also illustrated at a lowest point of sloped structure 720 to adequately drain all of the liquid when evacuating central chamber 716, according to an embodiment.

Figure 7E:
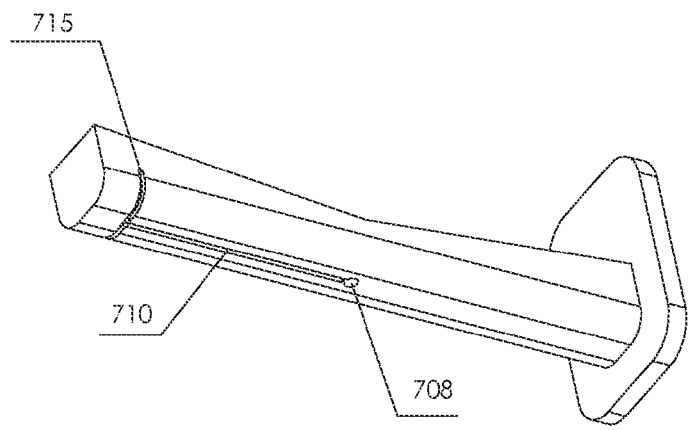

FIG. 7E illustrates another view from below lid 506 that shows hole 708 and transfer channel 710, according to an embodiment. One example includes side channels 715 to align the liquid with ports 712a and 712b on the sides of transfer module 504. The illustrated channel configurations are just one example for directing fluid into and out of central chamber 716 and should not be considered limiting.

Figure 7F:
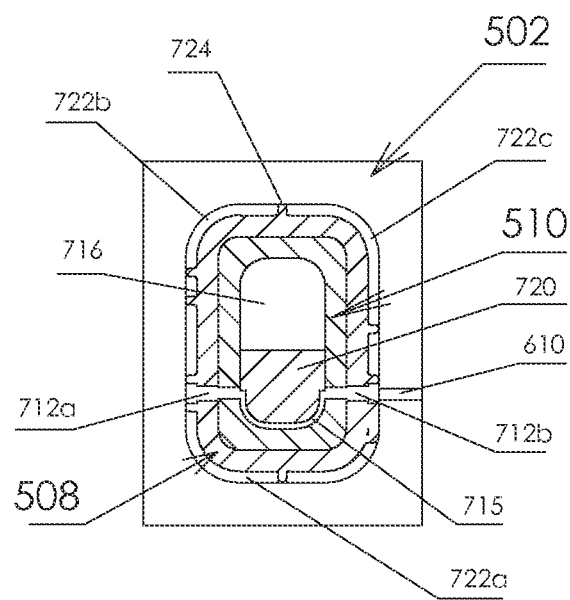

FIG. 7F illustrates a cross section view of transfer module 504 along a width of transfer module 504, according to an embodiment. Jacket 508 is observed wrapping around inner housing 510. Jacket 508 includes various protrusions 724, according to an embodiment. Protrusions 724 may represent the various patterned structures on jacket 508. In one example, protrusions 724 press against the inner walls of housing 502 to create various regions 722a, 722b, and 722c. Each region may be separately pressurized based on a position of transfer module 504 within housing 502. Ports 712a and 712b are illustrated as being aligned with one of ports 610 of housing 502 and a port associated with pressure port 636 respectively, according to an embodiment. As transfer module 504 moves laterally within housing 502, ports 712a and/or 712b may align with different ports 610 of housing 502. Also illustrated within central chamber 716 is sloped structure 720 and side channel 715, according to an embodiment. In the example embodiment, side channel 715 connects to each of ports 712a and 712b in a U-shape.

Figure 8A:
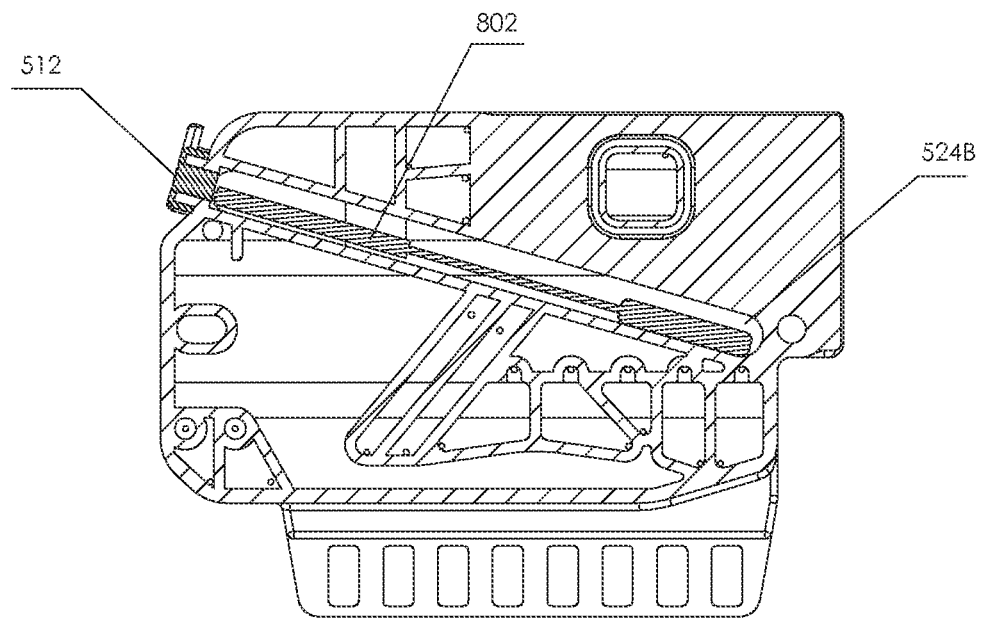
Figure 8B:
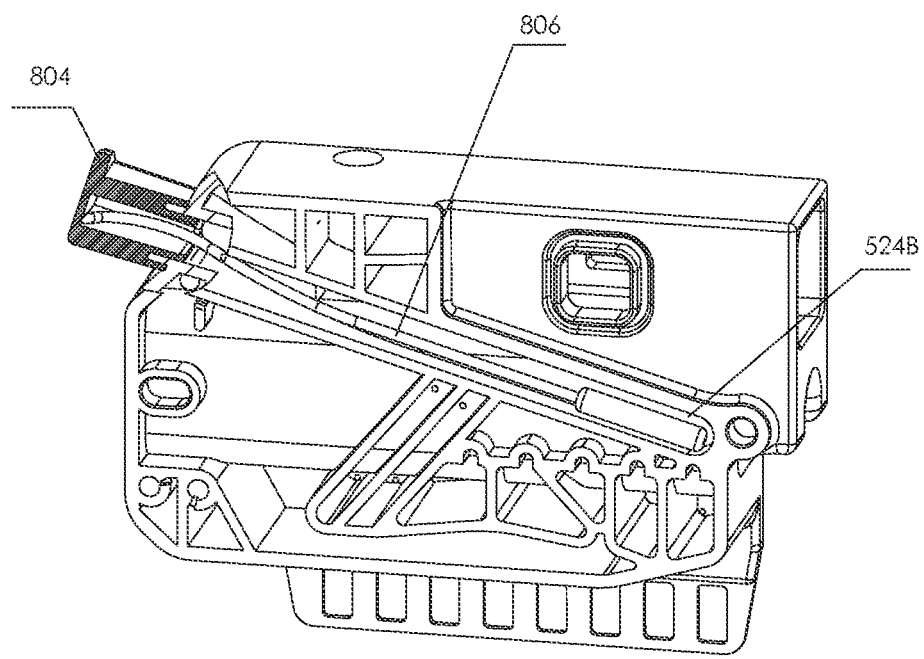

FIGS. 8A and 8B illustrate swabs being placed into the test cartridge system for analysis, according to some embodiments. FIG. 8A illustrates a swab 802 placed within chamber 524b of the cartridge housing. The chamber is sealed with port lid 512. In one example, swab 802 has a length around 80 mm. It should be understood that chamber 524b may be dimensioned to receive any length of swab without deviating from the scope or spirit of the invention.

FIG. 8B illustrates another embodiment where a longer swab 806 is placed into chamber 524b and sealed with an extended lid 804. Extended lid 804 may be used to seal over swabs that are longer than chamber 524b, and stick out from the chamber opening. In one example, longer swab 806 is around 100 mm in length. Longer swab 806 may be curved and/or bent within chamber 524b.

Exemplary Methods of Operation

Example methods for performing fluid transfer between various chambers of both embodiments of the cartridge housing and its corresponding transfer chamber are described below.

FIG. 9 displays a flowchart of an example method 900 for transporting liquid through a first embodiment of test cartridge system 100. It should be understood that method 900 describes one example operation sequence that can be performed with test cartridge system 100, and should not be considered limiting. Furthermore, method 900 may also be performed using the second embodiment of test cartridge system 500.

At block 902, transfer module 104 is laterally moved within cartridge housing 102 to align an inlet port of transfer module 104 to an outlet port of a first chamber, according to an embodiment. The inlet port of transfer module 104 may be, for example, primary inlet port 306. The outlet port of the first chamber may be, for example, any one of the row of inlet ports 228.

At block 904, a sample is drawn from the first chamber into transfer chamber 316 via an applied first pressure differential, according to an embodiment. In an embodiment, the applied pressure differential is applied at transfer pressure port 308. The applied pressure differential may be a vacuum pressure in order to draw the sample into transfer chamber 316. The sample may be introduced to the first chamber from a cotton swab or a liquid. The first chamber may be, for example, the inner processing chamber or a processing chamber associated with sample port 114. Additionally, the sample may be any mixture of liquids, semi-solids, solids, etc.

At block 906, transfer module 104 is laterally moved again within cartridge housing 102 to align an outlet port of transfer chamber 316 with an inlet port of a second chamber, according to an embodiment. The outlet port of transfer chamber 316 may be, for example, primary outlet port 312. The inlet port of the second chamber may be, for example, any one of the row of liquid ports 210. As such, the inlet port of the second chamber may lead to any chamber of cartridge housing 102, such as waste chamber 218, reaction chamber 216, swab elution chamber 206, etc.

At block 908, the sample is drawn from transfer chamber 316 to the second chamber via an applied second pressure differential, according to an embodiment. The second pressure differential may be a positive pressure applied at transfer pressure port 308. Alternatively, the second pressure differential may be a vacuum pressure applied at a vent/suction port 212 to draw liquid into the chamber associated with the corresponding vent/suction port 212.

It should be understood that many more liquid drawing procedures may be performed as would be understood by one having skill in the relevant art(s) given the description herein. For example, after block 904, the transfer chamber may align its inlet port to a second outlet port along the top of cartridge housing 102 to draw in another liquid stored in another storage chamber. This procedure may be repeated as many times as desired depending on the protocol necessary for the particular molecular test.

In another embodiment, following block 908, further steps may be performed to draw the sample back into the transfer chamber, and expel the liquid into a third chamber. For example, the second chamber may be swab elution chamber 206 while the third chamber may be one of detection chambers 216. Any number of chambers may have liquid drawn into or extracted out of as many times as desired. Thus, the system allows for a myriad of liquid transfer patterns amongst the various chambers.

FIG. 10 displays a flowchart of an example method 1000 for transporting liquid through a second embodiment of test cartridge system 500. It should be understood that method 1000 describes one example operation sequence that can be performed with test cartridge system 500, and should not be considered limiting.

At block 1002, transfer module 504 is laterally moved within cartridge housing 502 to align a structure on an outer surface of transfer module 504 to at least a first port associated with a first chamber and to a second port associated with a second chamber, according to an embodiment. The first chamber may be, for example, input reservoir 622 while the second chamber may be any of storage reservoirs 630a-g. The structure on the outer surface of transfer module 504 may have a toroid shape to fit around both the first and second ports, according to an embodiment.

At block 1004, a sample is drawn from the first chamber to the second chamber via at least the structure on the outer surface of transfer module 504, according to an embodiment. In this way, the sample may move between the first and second chamber without passing through, for example, a central chamber of transfer module 504.

At block 1006, the sample is drawn from the second chamber to a third chamber, according to an embodiment. The third chamber may be central chamber 716 of transfer module 504, and the liquid may enter central chamber 716 via a port through a wall of transfer module 504. The port may be, for example, any of fluid ports 706, 712a or 712b illustrated in FIGS. 7A and 7B. The third chamber may include components for mixing or filtering the sample. In other embodiments, transfer module 504 may move laterally to align a port of transfer module 504 to another port of housing 502 and expel the sample within its central chamber through the aligned port. It should be understood that many more liquid drawing procedures may be performed as would be understood by one having skill in the relevant art(s) given the description herein.

EXAMPLES

Two example protocols to be performed using test cartridge system 100 are now discussed. The first example protocol is directed to real-time PCR detection, while the second example protocol is directed to an immunoassay. It should be understood that the steps recited here provide possible examples for using the system, as well as for performing each test.

PCR Protocol

An example PCR protocol utilizes numerous processing chambers as well as reaction chambers around cartridge housing 102. In one example, the PCR protocol uses the cartridge housing embodiment illustrated in FIG. 2A. It should be understood that the protocol may also be performed using the cartridge housing embodiment illustrated in FIGS. 6A-6B. In this example, five storage chambers are used and each contains a pre-loaded solution. The storage chambers are labeled as such:

R1: Contains a wash-2 buffer
R2: Contains a lysis buffer
R3: Contains an elution buffer
R4: Contains a wash-3 buffer
R5: Contains a wash-1 buffer The example PCR procedure may be carried out using the workflow described herein with reference to example test cartridge system 100 described above. Similar steps may be performed using the various chambers and channels illustrated on test cartridge system 500 as well. The sample is introduced into test cartridge system 100 via a swab into swab receptacle 114. Alternatively, the sample may be introduced via a second inlet directly into an inner processing chamber to be lysed by an integrated bead beater system.

Once the sample has been introduced into test cartridge system 100, the entire test cartridge is placed into an analyzer. The analyzer provides an actuator for moving transfer module 104, one or more heating elements to perform the PCR reaction, and optical measurement components. The analyzer may further couple to the pressure ports around cartridge housing 102 and apply the necessary pressure differentials.

Transfer module 104 is aligned to draw in lysis buffer from R2 into the transfer chamber. Transfer module 104 is aligned to move the lysis buffer to the swab elution chamber 206, where the sample from the swab is re-suspended in the lysis buffer. The sample, along with the lysis buffer, may then be moved into the inner processing chamber via processing ports 204 to perform lysis on the cells in the sample and release the DNA and/or RNA. Following the lysing procedure, the sample is hereafter referred to as "the lysate."

The lysate is drawn back into the transfer chamber from the inner processing chamber via a vacuum pressure applied at the transfer chamber. Then, transfer module 104 is laterally moved to align its output port to a port associated with the waste chamber. However, a filter is disposed upstream from the waste chamber in order to capture the DNA sequences. Thus, after applying positive pressure to the transfer chamber, the lysate passes through the filter on its way to the waste chamber. The DNA will remain within the filter, while the bulk of any unwanted matter will pass through to the waste chamber. The filter may be, for example, a silicate matrix or a plurality of silica beads for entrapping the nucleic acid sequences.

Transfer module 104 is moved to align with R5 and draw wash-1 buffer into the transfer chamber. Subsequently, wash-1 buffer is passed through the filter to further remove any unwanted material in the filter. The buffer passes on to the waste chamber. A second wash step is then performed with the wash-2 buffer. Transfer module 104 aligns with R1 to draw in wash-2 buffer and moves again to align back with the fluidic channel containing the filter. Wash-2 is passed through the filter and on to the waste chamber.

At this stage, it may be required to clean the transfer chamber before the DNA can be brought back into it. As such, transfer module 104 is aligned with R4 and the wash-3 buffer is drawn into the transfer chamber. The wash buffer may be mixed around in the transfer chamber. Additionally, the wash-3 buffer may be transferred, for example, to the inner processing chamber.

Transfer module 104 is laterally moved to align its top inlet port to the outlet port of R3. A vacuum pressure is applied to draw the elution buffer into the transfer chamber. Afterwards, transfer module 104 is laterally moved to align its outlet port to the port associated with elution chamber 220 on cartridge housing 102. The elution buffer is moved into elution chamber 220 via an applied positive pressure to the transfer chamber or via a vacuum pressure from a vent/suction port connected to elution chamber 220.

The DNA is now ready to be removed from the filter and brought back into the transfer chamber. The elution buffer from elution chamber 220 of cartridge housing 102 is drawn through the filter using vacuum pressure back into the transfer chamber that is aligned to the correct port for receiving the DNA solution. Transfer module 104 may now sequentially move between the ports of the various reaction chambers and, via an applied positive pressure, transfer liquid into each chamber.

Each reaction chamber may contain a reagent necessary for performing PCR with the DNA. In an embodiment, the reagent is a pre-loaded, freeze-dried pellet which contains any reagents necessary for performing PCR. The reagents will quickly rehydrate when the DNA solution is brought into each chamber.

Once the DNA solution has been finally transferred into one or more of the reaction chambers, the rest of the process may be performed by the analyzer. That is, cycling of heating and cooling steps in order to at least one of activate, denature, anneal, and extend the DNA may be performed. Once the cycling is complete, the optical measurement system of the analyzer can collect data from each reaction chamber to provide test results to the end user.

Immunoassay

An example immunoassay utilizes at least three of the storage chambers as well as a variety of processing chambers around cartridge housing 102. In one example, the immunoassay uses the cartridge housing embodiment illustrated in FIG. 2B. Similar to a PCR protocol, the storage chambers contain pre-loaded solutions for performing the assay. Additionally, specific capture antibodies may be immobilized within the detection chambers 226 to provide binding sites to the antigens of interest. Fluorescently-labeled antibodies may also be pre-loaded in a lyophilized state into reaction chamber 224. In this example, the storage chambers are labeled as such:

R1: Wash-1 buffer
R2: Assay buffer
R3: Wash-2 buffer

The immunoassay may be carried out using the workflow described herein with reference to example test cartridge system 100 for clarity. The sample may be introduced into cartridge housing 102 through an inlet which leads directly to an inner processing chamber. Once introduced, test cartridge system 100 is placed into the analyzer. The rest of the protocol may be performed automatically by the analyzer system. Transfer module 104 is laterally aligned with the inner processing chamber and the sample is drawn into the transfer chamber via an applied vacuum pressure.

Once the sample is inside the transfer chamber, transfer module 104 laterally moves again to align its output port to a port which leads to the elution chamber. The sample from the elution chamber is then moved to the transfer chamber by passing through a membrane for obtaining plasma from whole blood. Once the plasma sample (containing the antigen of interest) is back in the transfer chamber, transfer module 104 may align with R2 and draw the assay buffer into the transfer chamber. The assay buffer and the plasma sample are mixed in the transfer chamber.

Once the plasma sample and the assay buffer are mixed, transfer module 104 laterally moves again to align its output port to a port which leads to reaction chamber 224, with the lyophilized fluorescently labeled antibodies. The sample+ assay buffer mixture acts to rehydrate the fluorescently labeled antibodies within reaction chamber 224. The rehydrated fluorescent antibodies, the sample plasma, and the assay buffer are all combined and mixed together. At this stage, if the antigen of interest is present in the mixture, the fluorescently labeled antibodies will have bound to it. In an embodiment, heating and/or mixing may be performed to enhance the reaction.

The resultant mixture is transported from reaction chamber 224 to each of detection chambers 226. Once again, the mixture may be gently mixed or heated in each detection chamber 226 to ensure interaction between the immobilized capture antibodies and the antigen within the mixture.

Once mixing is complete, transfer module 104 aligns with R1 and draws the wash-1 buffer into the transfer chamber. The wash-1 buffer may be first transferred into the reaction chamber and subsequently into each detection chamber containing the mixture. The wash-1 buffer clears away any unbound material. The wash-1 buffer continues through the detection chambers and passes into the waste chamber.

A second wash step may be performed. Transfer module 104 aligns with R3 and draws the wash-2 buffer into the transfer chamber. The wash-2 buffer may be first transferred into the reaction chamber and subsequently into each detection chamber containing the mixture. The wash-2 buffer clears away any unbound material. The wash-2 buffer continues through the detection chambers and passes into the waste chamber. At this stage, any bound material to the immobilized antibodies should be the antigen of interest along with the bound, fluorescently labeled antibody.

The optical measurement system of the analyzer can now be used for each detection chamber to quantify the amount of antigen based on the received fluorescent signal. The data collected may, for example, be plotted against a standard curve performed previously with calibrators to obtain the quantitative results for the end user.

It should be appreciated that at the end of either protocol discussed above, the entire test cartridge system 100 may be removed from the analyzer and safely disposed of. In another embodiment, the resultant solution within one or more of the detection chambers may be extracted for further analysis. Since the system is self-contained, numerous test cartridges may be used with the same analyzer without concern for cross-contamination or fouling between experiments.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A transfer module configured to store and transport liquid samples, comprising:
    an inner housing enclosing a central chamber;
    a jacket formed around the inner housing, the jacket comprising:
        patterned ridges along the outer surface of the jacket, wherein the patterned ridges are configured to define a plurality of valve regions along the outer surface of the jacket when the transfer module is disposed within an enclosure that comes into contact with the patterned ridges; and
        a plurality of ports extending through the jacket and the inner housing into the central chamber,
    wherein one of the plurality of valve regions is configured to be pressurized separately from other regions in the plurality of valve regions.

2. The transfer module of claim 1, wherein a flow of fluid occurs either into or out of the central chamber via one or more of the plurality of ports when one of the plurality of valve regions is pressurized.

3. The transfer module of claim 1, wherein the patterned ridges are further configured to define an area on the outer surface of the jacket that aligns with at least two ports of a housing substantially surrounding the transfer module and allow for fluid to flow between the at least two ports.

4. The transfer module of claim 1, wherein the inner housing and the jacket are formed as a single injection molded unit.

5. The transfer module of claim 1, wherein the plurality of ports are arranged along a side of the transfer module and along a top of the transfer module.

6. The transfer module of claim 1, wherein a plurality of the patterned ridges have a toroid shape.

7. The transfer module of claim 1, wherein at least one of the plurality of ports is located substantially at a lowest point in the central chamber.

8. The transfer module of claim 7, wherein walls of the central chamber are sloped to adequately drain a liquid within the central chamber through the at least one of the plurality of ports.

9. The transfer module of claim 1, further comprising a stir bar disposed within the central chamber.

10. The transfer module of claim 1, further comprising a lid configured to seal one end of the central chamber and having a sloped structure within the central chamber.

11. The transfer module of claim 10, wherein the sloped structure comprises a plurality of channels configured to direct liquid within the central chamber to one or more of the plurality of ports.

* * * * *